US011490973B2

(12) United States Patent
Penny et al.

(10) Patent No.: US 11,490,973 B2
(45) Date of Patent: Nov. 8, 2022

(54) ENDOSCOPY SYSTEM

(71) Applicant: EndoMaster Pte Ltd., Singapore (SG)

(72) Inventors: Isaac David Penny, Singapore (SG); Tae Zar Lwin, Singapore (SG); Jen Hui Teo, Singapore (SG)

(73) Assignee: ENDOMASTER PTE LTD, Singapore (SG)

( * ) Notice: Subject to any disclaimer, the term of this patent is extended or adjusted under 35 U.S.C. 154(b) by 191 days.

(21) Appl. No.: 16/757,223

(22) PCT Filed: Nov. 9, 2018

(86) PCT No.: PCT/SG2018/050563
§ 371 (c)(1),
(2) Date: Apr. 17, 2020

(87) PCT Pub. No.: WO2019/093968
PCT Pub. Date: May 16, 2019

(65) Prior Publication Data
US 2020/0315716 A1 Oct. 8, 2020

(30) Foreign Application Priority Data

Nov. 9, 2017 (SG) .......................... 10201709245X

(51) Int. Cl.
*A61B 1/00* (2006.01)
*A61B 34/37* (2016.01)
(Continued)

(52) U.S. Cl.
CPC .......... *A61B 34/30* (2016.02); *A61B 1/00128* (2013.01); *A61B 34/37* (2016.02);
(Continued)

(58) Field of Classification Search
CPC ................ A61B 1/00128; A61B 34/30; A61B 2034/301; A61M 2025/0059
See application file for complete search history.

(56) References Cited

U.S. PATENT DOCUMENTS

| 2007/0016067 A1 | 1/2007 | Webster, III et al. |
| 2008/0051629 A1 | 2/2008 | Sugiyama et al. |

(Continued)

FOREIGN PATENT DOCUMENTS

| EP | 1514508 A1 | 3/2005 |
| EP | 2014218 B2 | 1/2009 |

(Continued)

OTHER PUBLICATIONS

International Search Report for corresponding International Patent Application No. PCT/SG2018/050563, dated Jan. 31, 2019.
(Continued)

*Primary Examiner* — Alexandra L Newton
*Assistant Examiner* — Rynae E Boler
(74) *Attorney, Agent, or Firm* — Crowell & Moring LLP

(57) ABSTRACT

An endoscope system is provided, which comprises an endoscope having a hollow tube formed therein, a flexible elongate member having a first end for operational control and a second distal end for operation of robotic members, one or more actuators coupleable to the flexible elongate member at the first end thereof, and an anti-buckling tube arranged with respect to the hollow tube at the first end of the endoscope to prevent buckling of the flexible elongate member during translation of the one or more actuators. Different embodiments are also disclosed, including an endoscope comprising one or more flexible tendons having a wire coil sheath which includes wire having a substantially rectangular cross section, or an endoscope comprising a rotational-motion transmitting device, one or more flexible (Continued)

tendons and one or more electrical wires having anti-kink support thereon, a coupling means constraining the robotic member to an asymmetric range of motion, or torque joint means comprising a centrally aligned pulley for coupling the robotic member.

10 Claims, 41 Drawing Sheets

(51) Int. Cl.
 *A61M 25/00* (2006.01)
 *A61B 34/30* (2016.01)
 *A61B 34/00* (2016.01)
(52) U.S. Cl.
 CPC ... *A61B 2034/301* (2016.02); *A61B 2034/742* (2016.02); *A61M 2025/0059* (2013.01)

(56) References Cited

U.S. PATENT DOCUMENTS

| | | |
|---|---|---|
| 2008/0051655 A1 | 2/2008 | Sato et al. |
| 2009/0018390 A1 | 1/2009 | Honda et al. |
| 2009/0287043 A1* | 11/2009 | Naito ............ A61B 34/70 600/104 |
| 2010/0280449 A1 | 11/2010 | Alvarez et al. |
| 2012/0065628 A1 | 3/2012 | Naito |
| 2012/0071895 A1* | 3/2012 | Stabler ............ A61B 8/4218 606/130 |
| 2016/0174956 A1 | 6/2016 | Ciulla et al. |
| 2016/0262595 A1 | 9/2016 | Kakehashi |

FOREIGN PATENT DOCUMENTS

| | | |
|---|---|---|
| EP | 2082679 A2 | 7/2009 |
| EP | 2594308 A1 | 5/2013 |
| EP | 3284389 A1 | 4/2016 |
| EP | 3369358 A1 | 9/2018 |
| JP | 2002-330923 A | 11/2002 |
| JP | 2004-033491 A | 2/2004 |
| JP | 2009-011809 A | 1/2009 |
| JP | 2016-537056 A | 12/2016 |
| WO | WO 2004/103430 A2 | 12/2004 |
| WO | WO 2013/106444 A1 | 7/2013 |
| WO | WO 2014/123245 A1 | 8/2014 |
| WO | WO 2016/037133 A1 | 3/2016 |
| WO | WO 2016/084092 A | 6/2016 |
| WO | WO 2016/185842 A1 | 11/2016 |
| WO | WO 2017/073187 A1 | 5/2017 |

OTHER PUBLICATIONS

Written Opinion for corresponding International Patent Application No. PCT/SG2018/050563, dated Feb. 11, 2019.
Japanese Office Action with English translation regarding 2020-524790 dated Sep. 20, 2022, 7 pages.

* cited by examiner

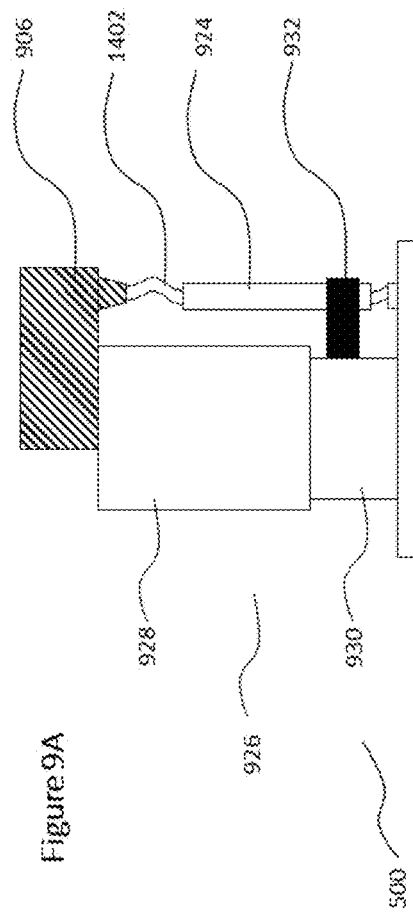
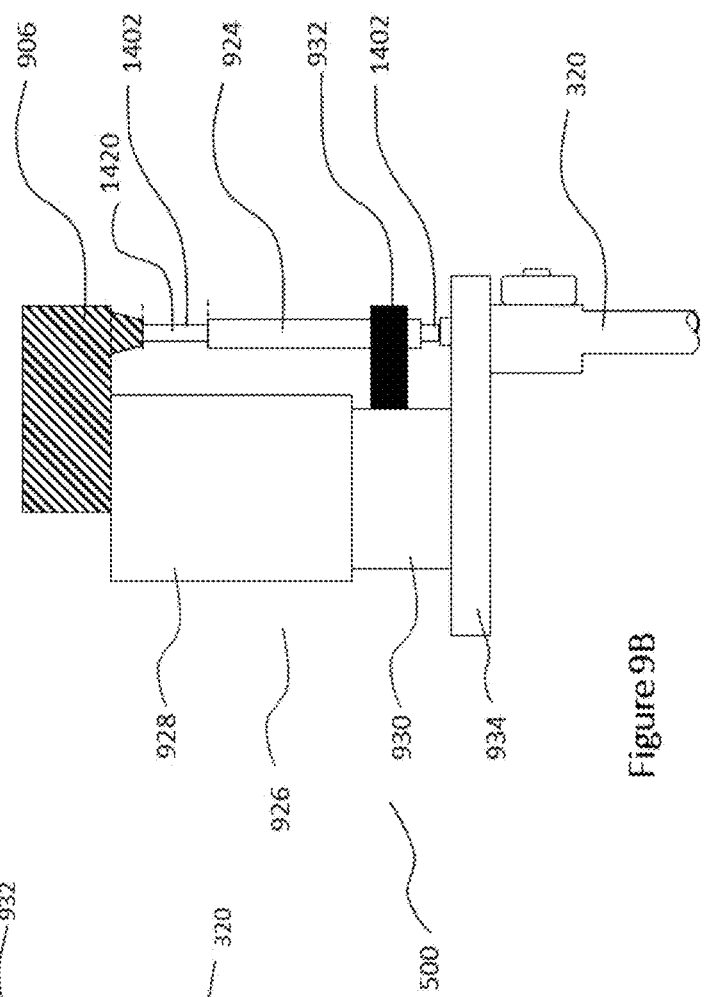

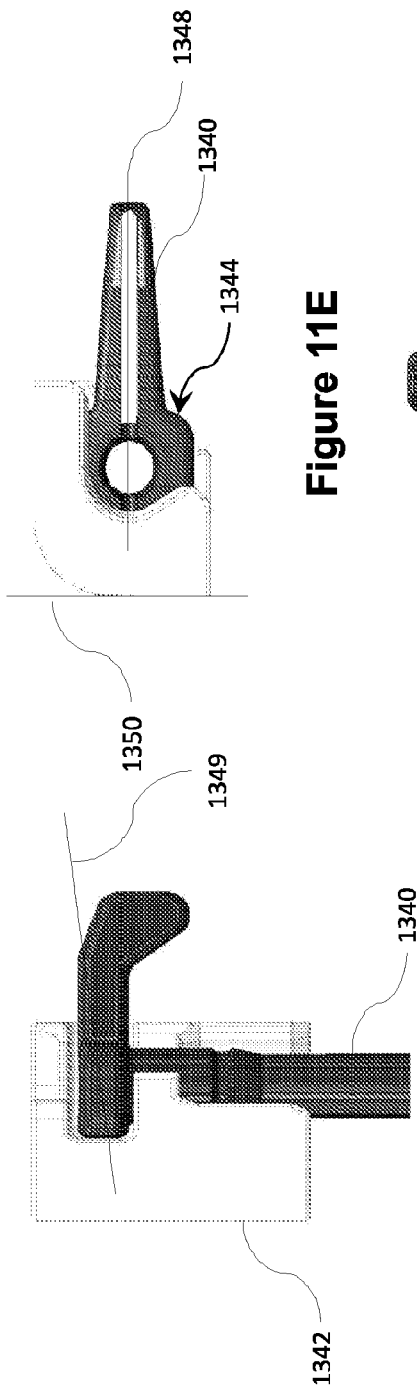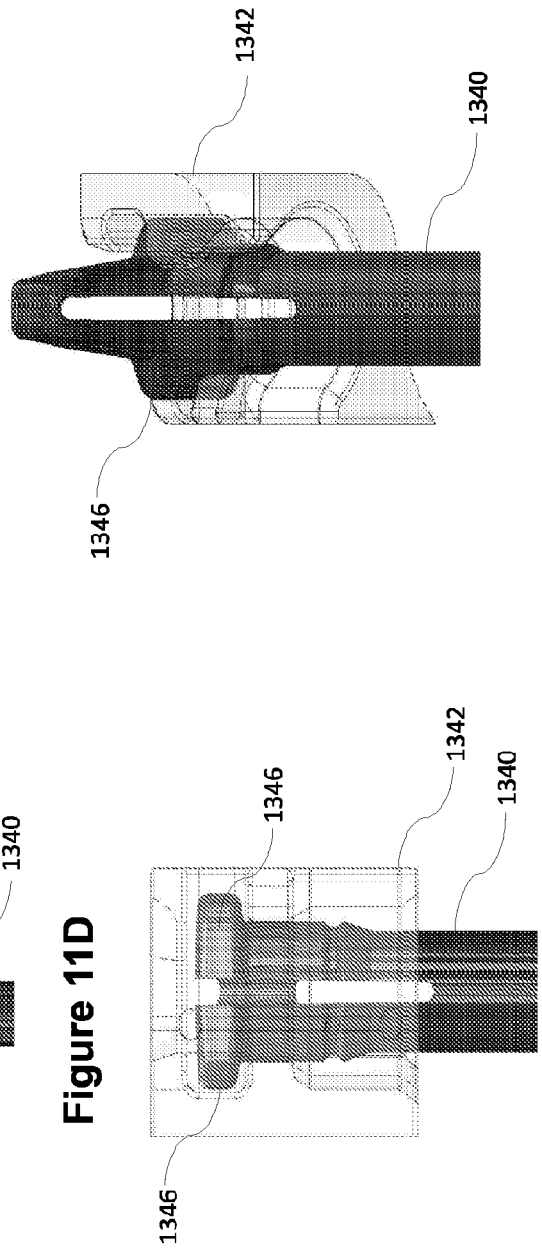
Figure 11D
Figure 11E
Figure 11F
Figure 11G

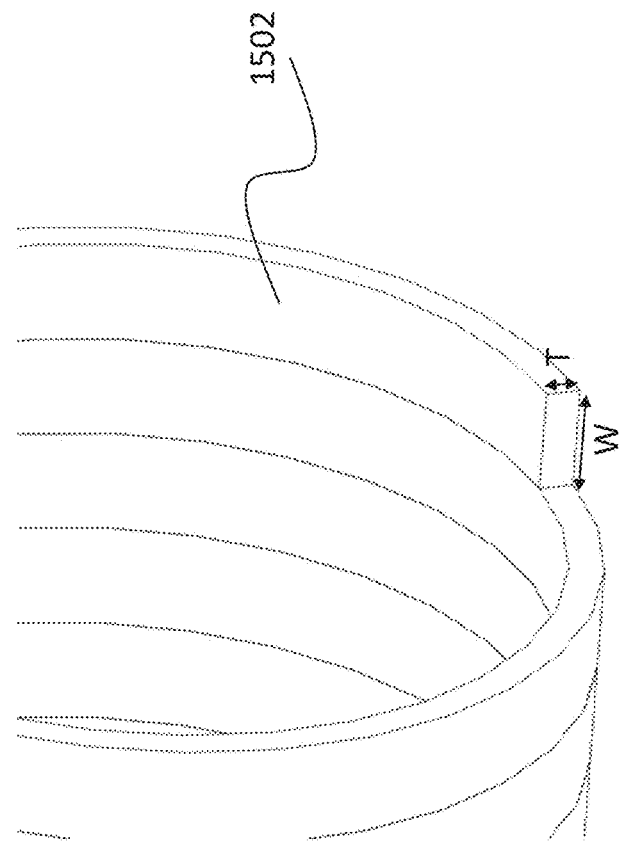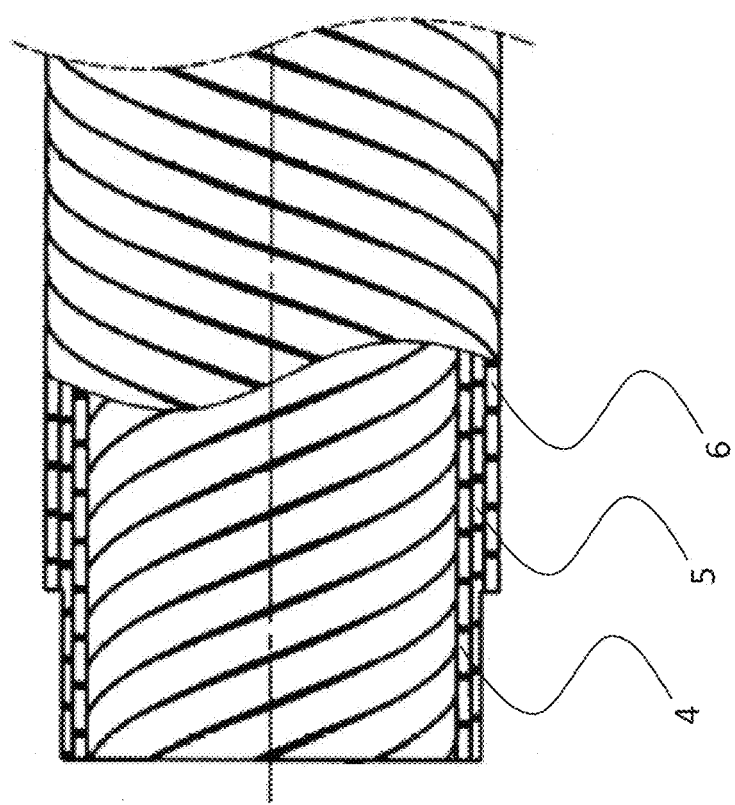
Figure 15

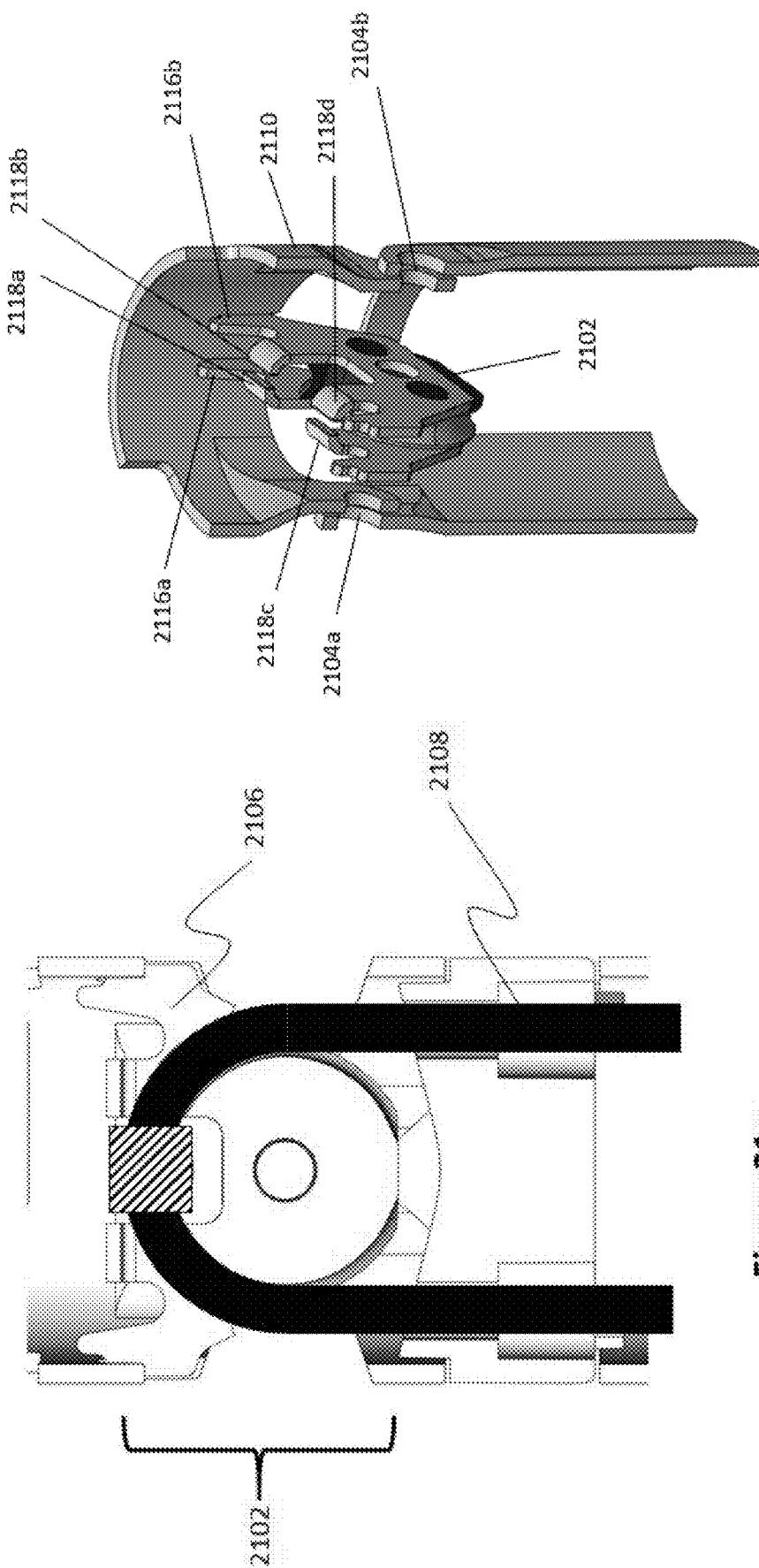

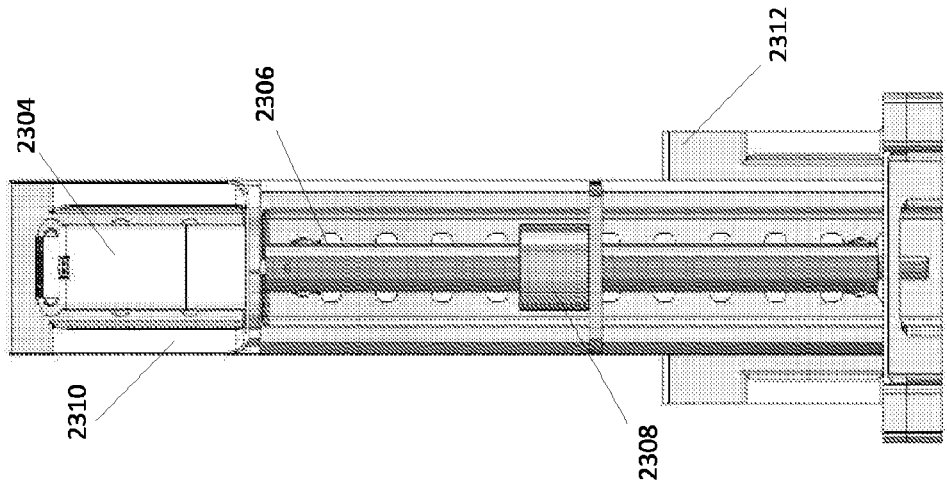
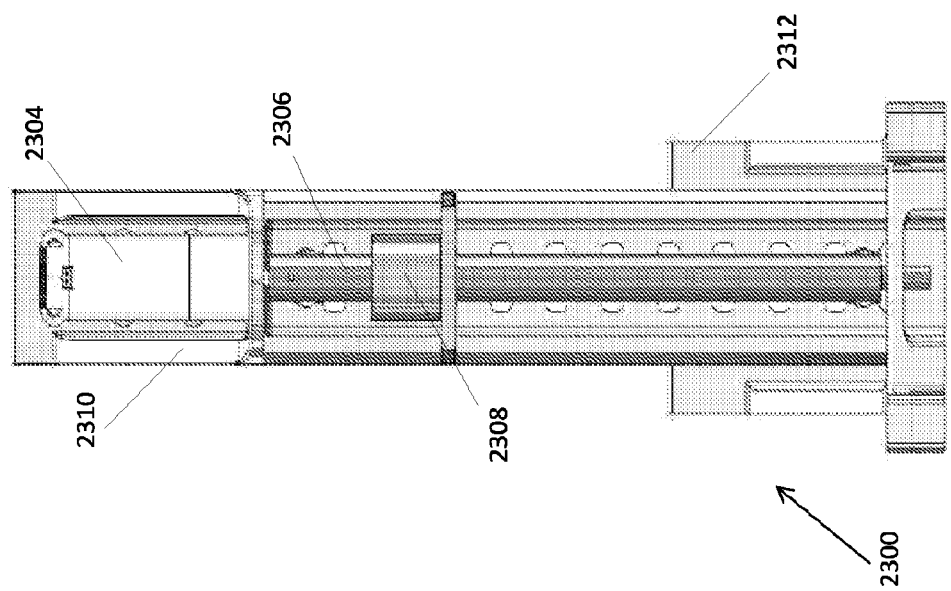
Figure 23e
Figure 23d

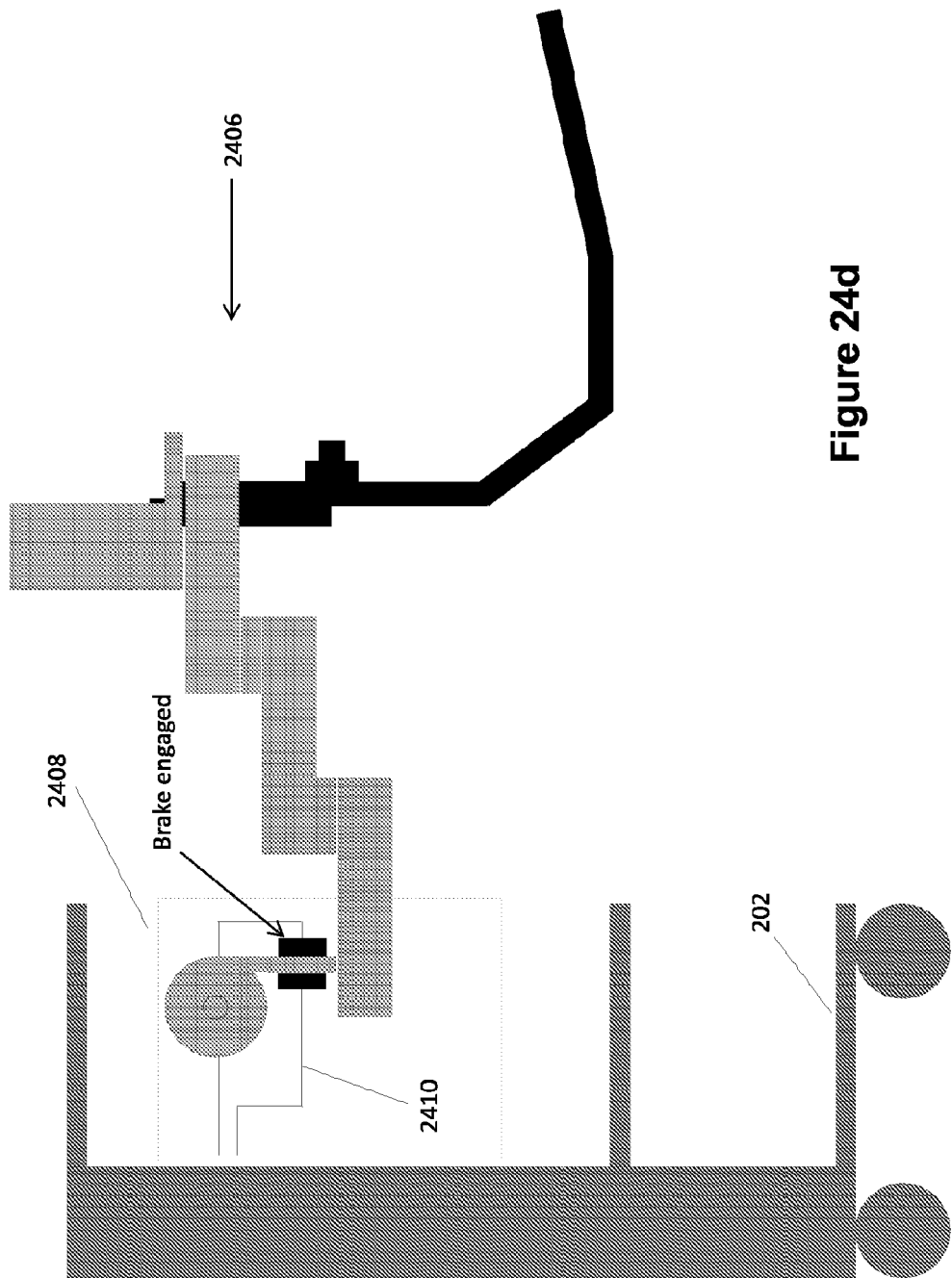

ENDOSCOPY SYSTEM

CROSS-REFERENCE TO RELATED APPLICATIONS

The present application is the U.S. National Stage application of PCT Application No. PCT/SG2018/050563, filed on Nov. 9, 2018, designating the United States, which claims priority from Singapore Patent Application No. 10201709245X filed on Nov. 9, 2017, the content of which is incorporated herein by reference.

TECHNICAL FIELD

The present invention relates generally, but not exclusively, to an endoscopy system.

BACKGROUND OF THE DISCLOSURE

An endoscope is a hollow tube which is used to examine and/or deliver an instrument to an interior of a hollow organ or cavity of a body. For example, an endoscope can be used to examine the upper gastrointestinal tract (e.g., throat, esophagus or stomach) or the lower gastrointestinal tract (e.g. colon). The endoscope typically provides light to the internal area and provides vision for the endoscopist to navigate within the organ or cavity. Once an area is identified which needs treatment, an instrument necessary for treating the identified location is inserted into the hollow tube within the endoscope and maneuvered to the area. The instrument may, for example, be used to remove a polyp in the colon or to take a biopsy tissue sample from within the identified area for testing.

The instrument is a flexible elongate member which is fed through the hollow tube of the endoscope to the treatment site. In order for precision operation of the instrument, it is important to prevent kinking and buckling of the flexible elongate member. In some embodiments, a coil sheath is wrapped around the cables. However, a cable with a circular coil sheath, while sufficient to transmit compressive forces, is prone to buckle or kink when there is a high amount of bending on the wire coil sheath, resulting in a narrowing of the area inside the wire coil sheath. The narrowing of the lumen due to the buckling/kinking of the wire coil sheath results in increased friction between the cable and the wire coil sheath, reducing the force transmission efficiency of the cable.

Thus, what is needed is an endoscope device and an endoscope system for that overcomes the above drawbacks. Furthermore, other desirable features and characteristics will become apparent from the subsequent detailed description and the appended claims, taken in conjunction with the accompanying drawings and this background of the disclosure.

SUMMARY

According to an aspect of the present invention, an endoscope system is provided. The endoscope system includes an endoscope, a flexible elongate member, one or more actuators and an anti-buckling tube. The endoscope has a hollow tube formed therein and has a first end coupleable to a docking station and a second distal end. The flexible elongate member is insertable through the hollow tube of the endoscope and has a first end for operational control and a second distal end for operation of robotic members at the distal end of the endoscope. The one or more actuators are coupleable to the flexible elongate member at the first end and are translatable in a direction parallel to a central axis of the hollow tube to allow fine movement of the second distal end of the flexible elongate member during operation. And the anti-buckling tube is arranged with respect to the hollow tube at the first end of the endoscope such that the flexible elongate member is inserted through the anti-buckling tube downstream of the one or more actuators to prevent buckling of the flexible elongate member during translation of the one or more actuators.

According to a second aspect of the present invention, an endoscope system is provided which includes an endoscope and a flexible elongate member. The endoscope has a hollow tube formed therein for insertion of the flexible elongate member. The flexible elongate member has a first end for operational control and a second distal end for operation of robotic members at a distal end of the endoscope. The flexible elongate member also includes one or more flexible tendons to provide operational control from the first end to the robotic members at the second distal end, each of the one or more flexible tendons having a wire coil sheath which includes wire having a substantially rectangular cross section wound around a corresponding one of the one or more flexible tendons.

According to a third aspect of the present invention, a flexible elongate member for use in an endoscopy system is provided. The flexible elongate member has a first end for operational control and a second distal end for operation of robotic members at the second distal end. The flexible elongate member includes one or more flexible tendons to provide operational control from the first end to the robotic members at the second distal end. Each of the one or more flexible tendons has a wire coil sheath which includes wire having a substantially rectangular cross section wound around the corresponding one of the one or more flexible tendons.

According to a fourth aspect of the present invention, an endoscope system is provided. The endoscope system includes an endoscope and a flexible elongate member. The endoscope has a hollow tube formed therein for insertion of the flexible elongate member. The flexible elongate member has a first end for operational control and is coupled to robotic members at a distal end of the endoscope for operation thereof. The flexible elongate member includes a rotational-motion transmitting device forming a shaft of the flexible elongate member for propagating actuation from the first end to the robotic members at the second distal end.

According to a fifth aspect of the present invention, a flexible elongate member for use in an endoscopy system is provided. The flexible elongate member has a first end for operational control and is coupled to robotic members at a second distal end. The flexible elongate member includes a rotational-motion transmitting device forming a shaft of the flexible elongate member for propagating actuation from the first end to the robotic members at the second distal end.

According to a sixth aspect of the present invention, an endoscope system is provided. The endoscope system includes an endoscope, a flexible elongate member and at least one anti-kink support. The endoscope has a hollow tube formed therein for insertion of the flexible elongate member. The flexible elongate member has a first end for operational control and a second distal end for operation of robotic members at a distal end of the endoscope. The flexible elongate member including one or more flexible tendons to provide operational control from the first end to the robotic members at the second distal end. The at least one anti-kink support is located on one of the one or more flexible tendons to enforce a minimum bend radius on the one of the one or more flexible tendons, the anti-kink support pivoting freely about the one of the one or more flexible tendons.

According to a seventh aspect of the present invention, an endoscope system is provided. The endoscope system includes an endoscope, a flexible elongate member, at least one robotic member and coupling means for coupling the at least one robotic member to the flexible elongate member. The endoscope has a hollow tube formed therein. The flexible elongate member is insertable through the hollow tube and has a first end for operational control and a second distal end having a camera coupled thereto.

The at least one robotic member is located at the second distal end of the flexible elongate member and the coupling means couples the at least one robotic member to the flexible elongate member while constraining the robotic member to an asymmetric range of motion.

According to an eighth aspect of the present invention, an endoscope system is provided. The endoscope system includes an endoscope, a flexible elongate member, at least one robotic member and torque joint means for coupling the at least one robotic member to the flexible elongate member. The endoscope has a hollow tube formed therein. The flexible elongate member is insertable through the hollow tube and has a first end for operational control and a second distal end. The at least one robotic member is located at the second distal end of the flexible elongate member and the torque joint means includes a centrally aligned pulley.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with present embodiments.

FIGS. 9A and 9B show schematic illustrations of the components of a docking station of the endoscopy system of FIG. 1 in accordance with the present embodiment.

FIGS. 11D to 11G show various views of a further structure used to realize components of the docking station of the endoscopy system of FIG. 1 in accordance with the present embodiment.

FIG. 15 shows a cross section view of a shaft of the flexible elongate member of FIG. 14 in accordance with the present embodiment.

FIG. 21a shows a side view of a pulley in accordance with the present embodiment.

FIG. 21b shows a perspective view of a torque joint with the pulley in accordance with the present embodiment.

FIG. 23a shows a perspective view of a typical translation mechanism of FIGS. 12A and 12B while

FIGS. 23c, 23d and 23e show cross section views of an implementation of a translation mechanism in accordance with the present embodiment.

FIG. 24d shows a side view of the first implementation with an engaged electromagnetic brake when the endoscope docking system is at its highest position in accordance with the present embodiment.

Figure 1:
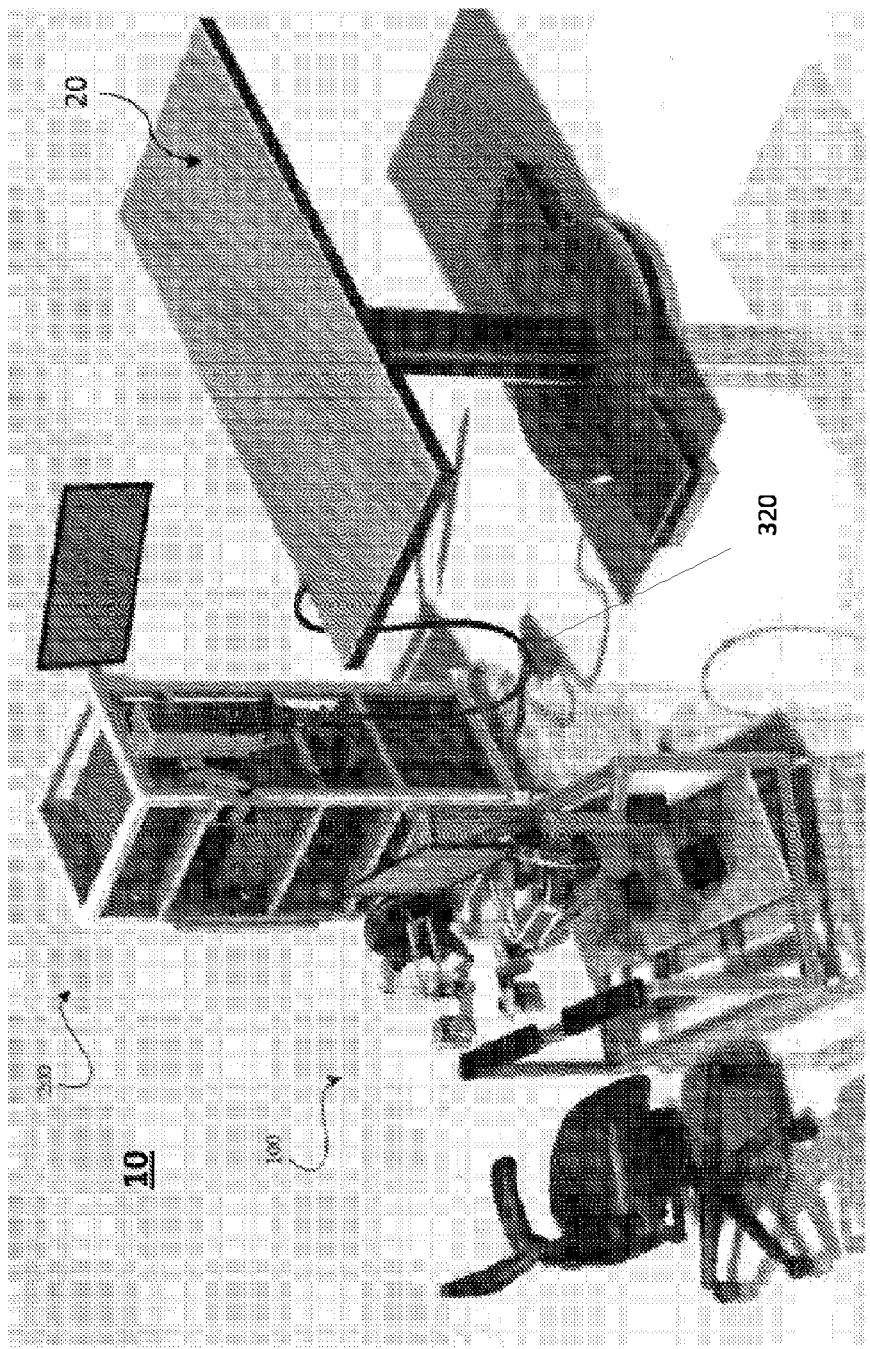
FIG. 1 shows a schematic illustration providing a perspective view of an endoscopy system in accordance with a present embodiment.

Example embodiments of the invention will be better understood and readily apparent to one of ordinary skill in the art from the following written description, by way of example only, and in conjunction with the drawings. The drawings are not necessarily to scale, emphasis instead generally being placed upon illustrating the principles of the invention.

DETAILED DESCRIPTION

In the following description, various embodiments are described with reference to the drawings, where like reference characters generally refer to the same parts throughout the different views.

FIG. 1 is a schematic illustration providing a perspective view of an endoscopy system 10. The endoscopy system 10 has a master or master-side section 100 having master-side elements and a slave or slave-side section 200 having slave-side elements.

Figure 2:
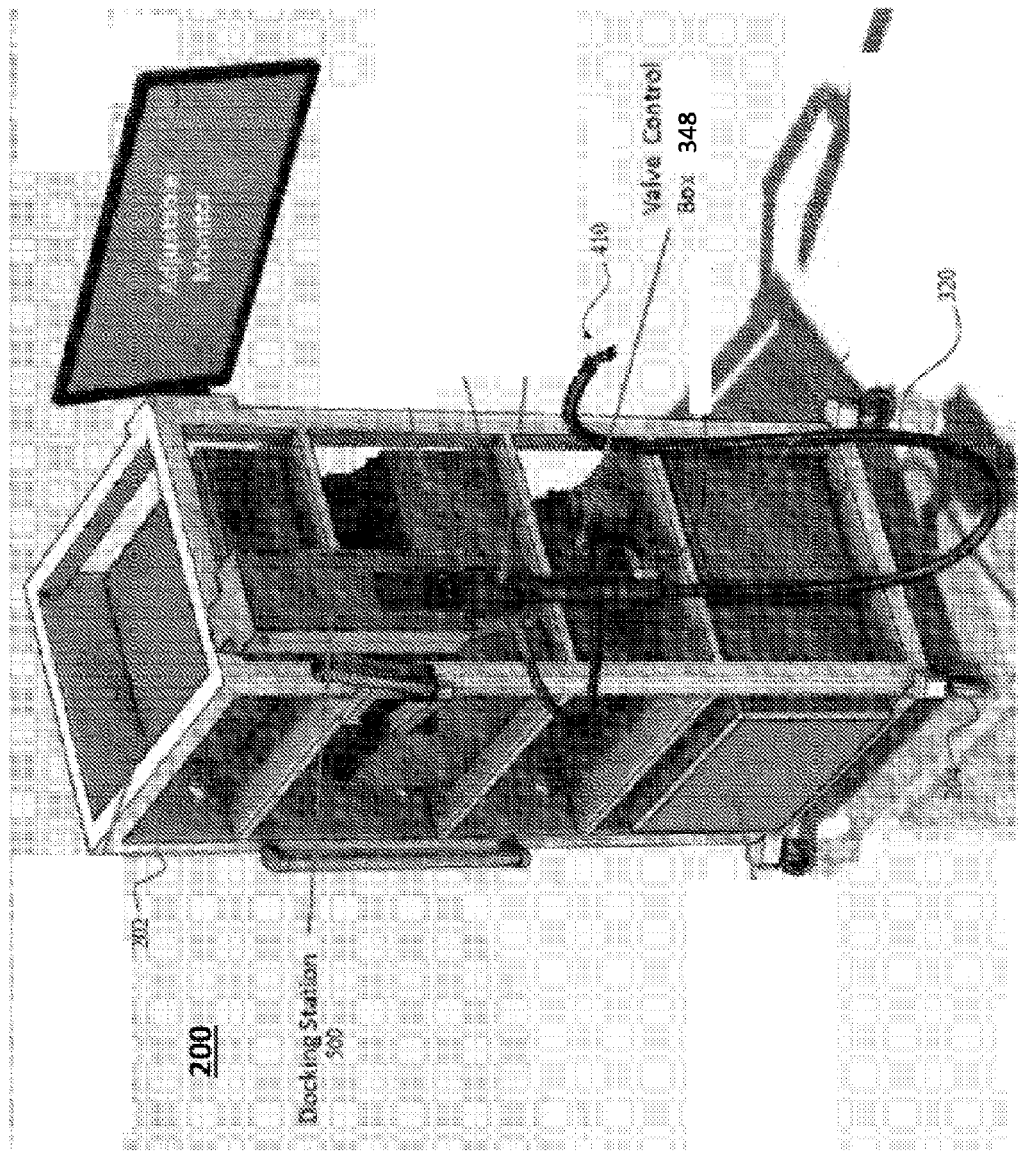
FIG. 2 shows a schematic illustration of a slave section of the endoscopy system of FIG. 1 in accordance with the present embodiment.
Figure 16:
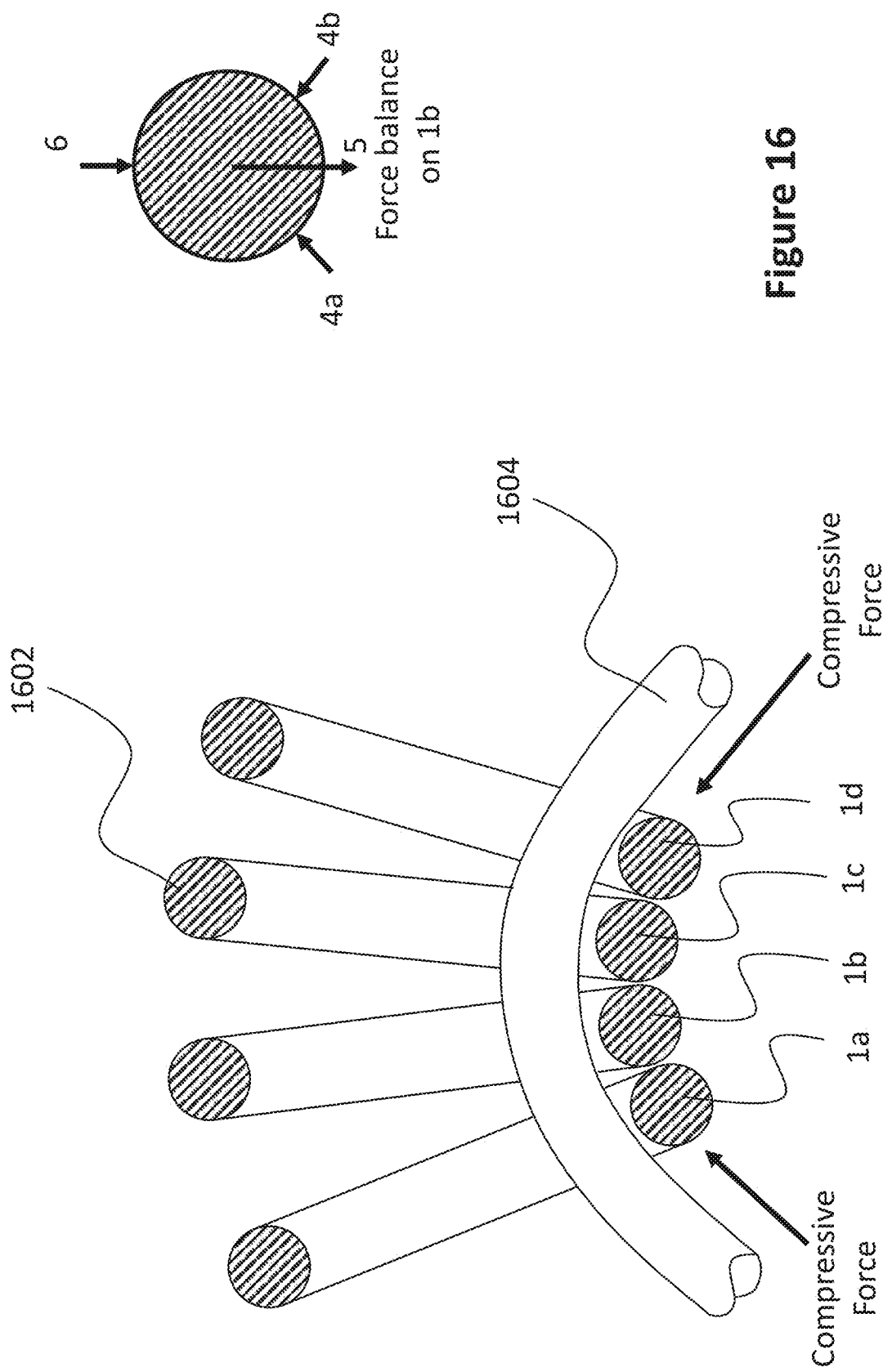
FIG. 16 shows a cross section view of a segment of a circular coil sheath in accordance with the present embodiment.
Figure 17:
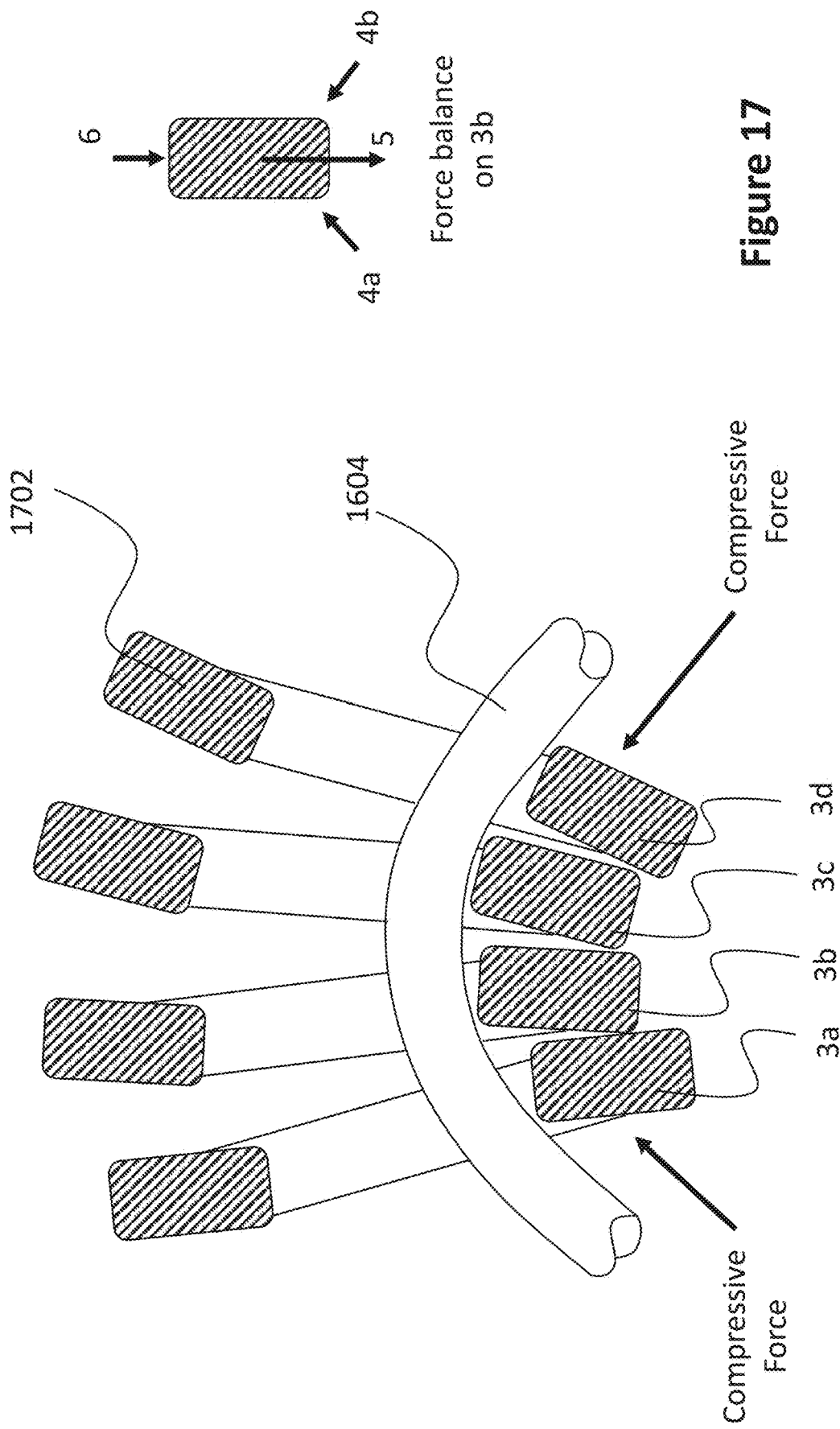
FIG. 17 shows a cross section view of a segment of a rectangular coil sheath in accordance with the present embodiment.
Figure 18:
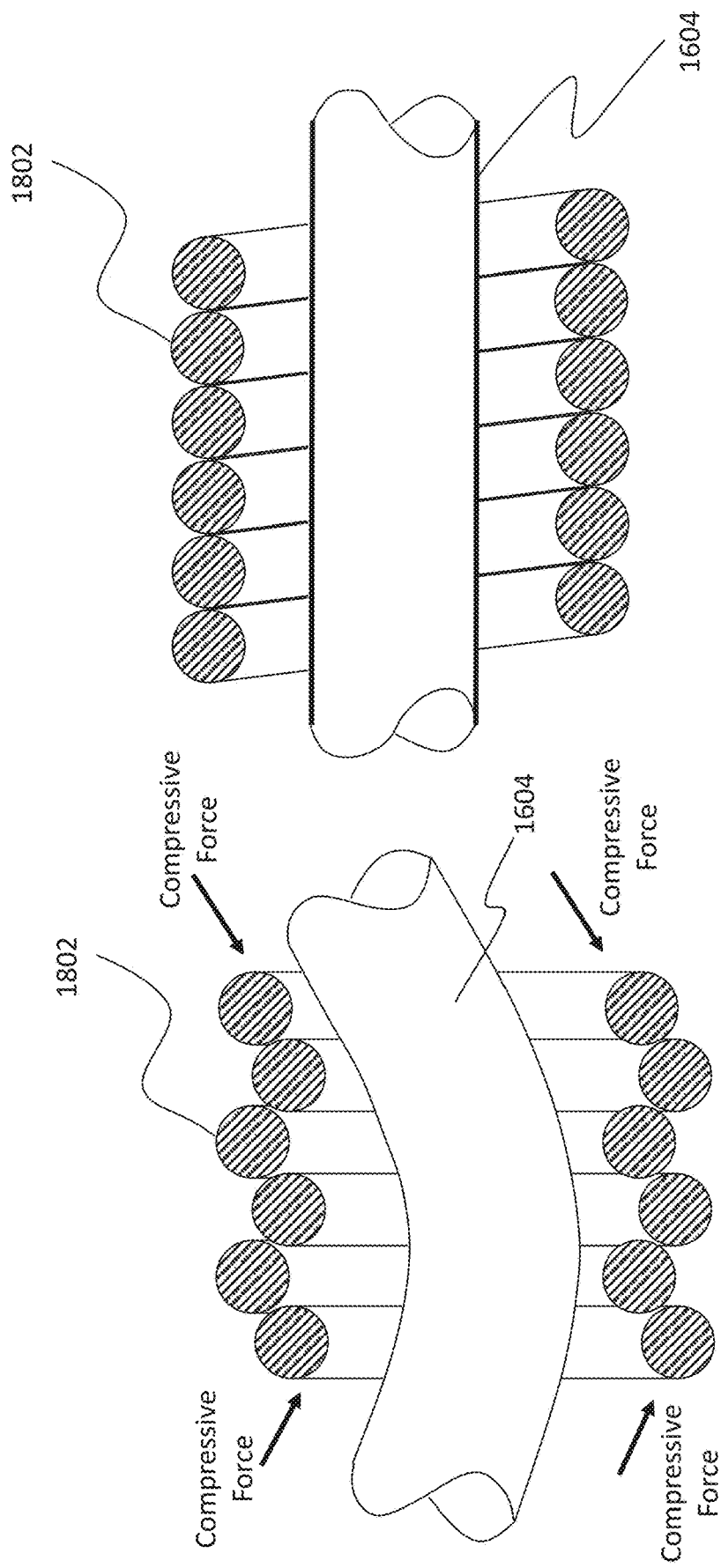
FIG. 18 shows a cross section view of the segment of the circular coiled wire sheath of FIG. 16 in accordance with a second embodiment.

With reference to FIG. 2, the master section 100 and the slave section 200 are configured for signal communication with each other such that the master section 100 can issue commands to the slave section 200 and the slave section 200 can precisely control, maneuver, manipulate, position, and/or operate, in response to master section 100 inputs, (a) a set of robotic members 410 carried or supported by a transport endoscope 320 of the slave section 200, the transport endoscope 320 having a flexible elongate shaft; (b) an imaging endoscope or imaging probe member carried or supported by the transport endoscope 320; (c) valves that are used to perform air or $CO_2$ insufflation, water irrigation and fluid suction, the valves being coupled to passage tubes that are carried or supported by the transport endoscope 320; and (d) a probe for surgical procedures, e.g. tissue manipulation or retraction, incision, dissection and/or hemostasis, by way of one or more of electrocauterization (using an electrocautery), or lasing (using a laser), where electrical wiring connecting to the probe is carried or supported by the probe or transport endoscope 320. The master and slave sections 100, 200 can further be configured such that the slave section 200 can dynamically provide tactile/haptic feedback signals (e.g., force feedback signals) to the master section 100 as the robotic members 410 are positioned, manipulated, or operated. Such tactile/haptic feedback signals are correlated with or correspond to forces exerted upon the robotic members 410 within an environment in which the robotic members 410 reside, such as an organism on an operating table 20. Robotic members 410 (see FIG. 14) refer to arms or grippers that can grab and lift tissue. Robotic members can optionally host an electrocautery probe for dissection of tissue or for hemostasis. Actuation of the arms or grippers is brought about by a cable pair (also referred to as a "tendon", of which one is shown in FIGS. 16, 17 and 18, denoted using the reference numeral 1604. The cable/tendon may be protected by a sheath, which is not shown in FIGS. 16, 17 and 18, but denoted using reference numeral 1602 in the cross-section view of FIG. 16a) internally located within a shaft (denoted using reference numeral 1402 in FIGS. 9A, 9B and 14). The shaft, which may be insulated by a protective cover 1606, is used to translate and/or rotate the arms or grippers. This shaft, internally located cable pairs, and protective cover are referred to as a flexible elongate member 1600 (see FIG. 16a). The cable pair serves to move joints of the arms or grippers so that the robotic members 410 can grab or dissect tissue, or for other medical purposes. The actuators for the cable pair are housed in a translatable motor housing (see reference numeral 926 in FIGS. 9A, 9B, 10, 11A, 12A and 12B) operably coupled to an adaptor (see reference numeral 906 in FIGS. 9A, 9B and 10). This adaptor 906, the flexible elongate member 1600 and the robotic members 410 are referred to as a surgical instrument, whereby the robotic members 410 are at the distal end of the surgical instrument.

FIG. 2 is a schematic illustration of the slave section 200 of the endoscopy system 10 of FIG. 1. The slave section 200 has a patient-side cart, stand, or rack 202 configured for carrying at least some slave section elements. The patient-side cart 202 has a docking station 500 to which the transport endoscope 320 can be detached (e.g., mounted/docked and dismounted/undocked) and an associated valve controller box 348. The patient side cart 202 typically includes wheels 204 to facilitate easy portability and positioning of the slave section 200.

Figure 3:
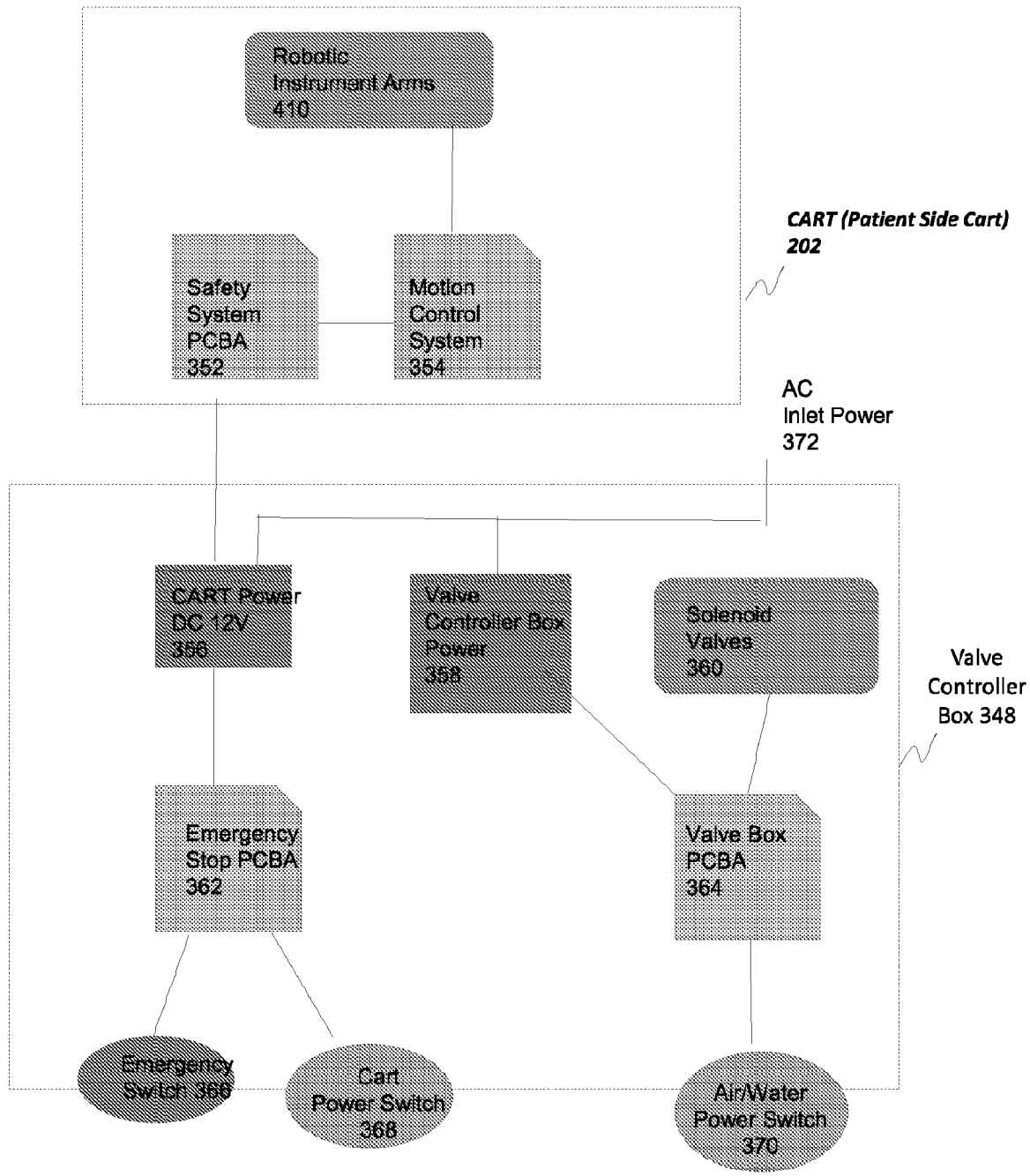
FIG. 3 shows a block diagram of modules located in either or both of a master section and a slave section of the endoscopy system of FIG. 1 in accordance with the present embodiment.

FIG. 3 shows a block diagram of modules located in either or both of the master section 100 and the slave section 200 of the endoscopy system 10 of FIG. 1. The air insufflation, water irrigation and fluid suction capabilities of the transport endoscope 320 of FIG. 2 are associated with these modules. The valve controller box 348 contains several of the modules, where the valve controller box 348 is located on the patient-side cart 202 shown in FIG. 2 or separate from, but in the vicinity of the patient-side cart 202. The remaining modules, a safety system module 352 and a motion control system module 354, are either located on the patient-side cart 202 or attached to slave-side elements located on the patient-side cart 202, such as the robotic members 410 being coupled to the translatable housing 926 that is a part of the docking station 500.

The modules located in the valve controller box 348 include a valve box printed circuit board assembly (PCBA) 364, an emergency stop PCBA 362, a cart power output port 356 (having a 12V rating), a valve controller box power module 358 (having a 24V rating), solenoid valves 360, an emergency switch 366, a cart power switch 368 and an air/water power switch 370.

The valve box PCBA 364 controls the solenoid valves 360 for the air insufflation, water irrigation and fluid suction functions of the transport endoscope 320. The emergency stop PCBA 362 controls the safety system module 352, which in turn controls the motion control system module 354. The motion control system module 354 controls the robotic members 410.

The valve controller box 348 has an AC inlet power port 372 which includes an AC to DC converter to provide a DC power supply to the cart power output port 356 and the valve controller box power module 358. The cart power output port 356 and the valve controller box power module 358 supply power to the emergency stop PCBA 362 and the valve controller box power module 358 respectively. The power is supplied to the emergency stop PCBA 362 and the valve controller box power module 358 when the cart power switch 368 and the air/water power switch 370 are switched on, respectively.

The electrical system for the modules shown in FIG. 3 is configured to have the circuitry connecting the solenoid valves 360, the valve controller box 348, the valve box PCBA 364 and the air/water power switch 370 electrically isolated from the circuitry to which the remainder of the modules belong. This configuration is such that when the emergency switch 366 is activated, the solenoid valves 360 will continue operating. The reason for keeping the solenoid valves 360 functioning is that activation of the emergency switch 366 should not introduce any harm during a surgical operation according to medical device safety standards.

In a first implementation, where both the cart power output port 356 and the valve controller box power module 358 are connected to the AC inlet power port 372, the cart power output port 356 and the valve controller box power module 358 are on parallel electrical connections with the AC inlet power port 372. Operation of the emergency stop PCBA 362 is also controlled by the emergency switch 366 in that activation of the emergency switch 366 cuts off power to the robotic members 410. This causes the robotic members 410 to stop operating, while the valve controller box power module 358 remains powered to allow the solenoid valves 360 to remain operating. Power cut off to the robotic members 410 can be done in one of several ways, such as: terminating the connection between the cart power output port 356 and the AC inlet power port 372; terminating the connection between the cart power output port 356 and the safety system module 352; or terminating the connection between the safety system module 352 and the motion control system module 354.

In a second implementation (not shown), the cart power output port supplies power to all components of the patient-side cart of the slave section 200 (see FIG. 2). In this second implementation, the cart power output port, along with its associated modules; and the valve controller box power module, along with its associated modules, are in separate enclosures. Each of these two enclosures is independently connected to the AC inlet power port so as to achieve electrical isolation.

Figure 4:
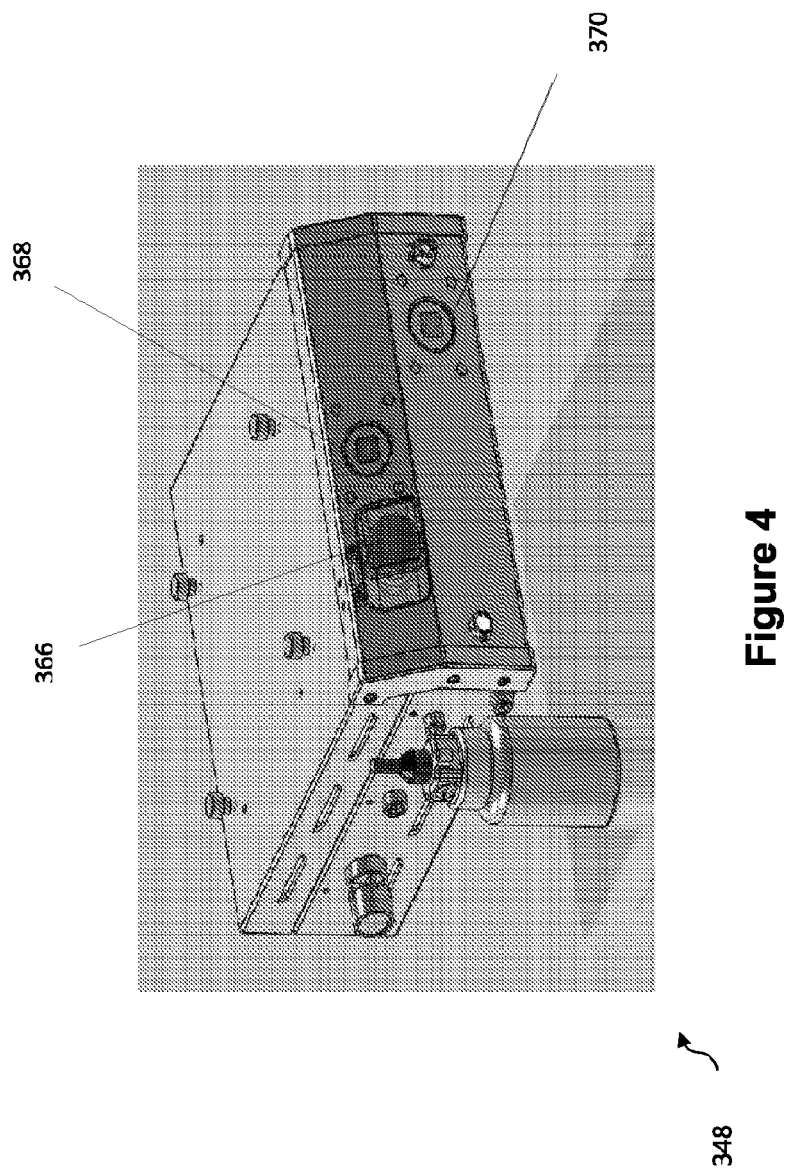
FIG. 4 shows a perspective view of a valve controller box in accordance with the present embodiment.

As the valve controller box power module 358 and the cart power output port 356 are independent from each other, due to the above-mentioned electrical isolation, power is still supplied to the valve controller box power module 358 even after cutting off power to the cart power output port 356. Thus, the solenoid valves 360 remain in operation and the air insufflation, water irrigation and fluid suction functions are unaffected, i.e. the passage tubes which are carried or supported by the transport endoscope 320 and are coupled to the solenoid valves 360 still carry air and water from the solenoid valves 360 to the organism on the operating table 20 and fluid from the organism to the solenoid valves 360. FIG. 3 is a schematic illustration providing a perspective view of the valve controller box 348 shown in FIG. 4.

The emergency switch 366, the cart power switch 368 and the air/water power switch 370 are located in the front of the valve controller box 348. The valve controller box 348 also has ports to which the safety system module 352 is connected; position input devices (PID) 702 (see FIG. 7) are connected; and a display 704 (see FIG. 7).

Figure 7:
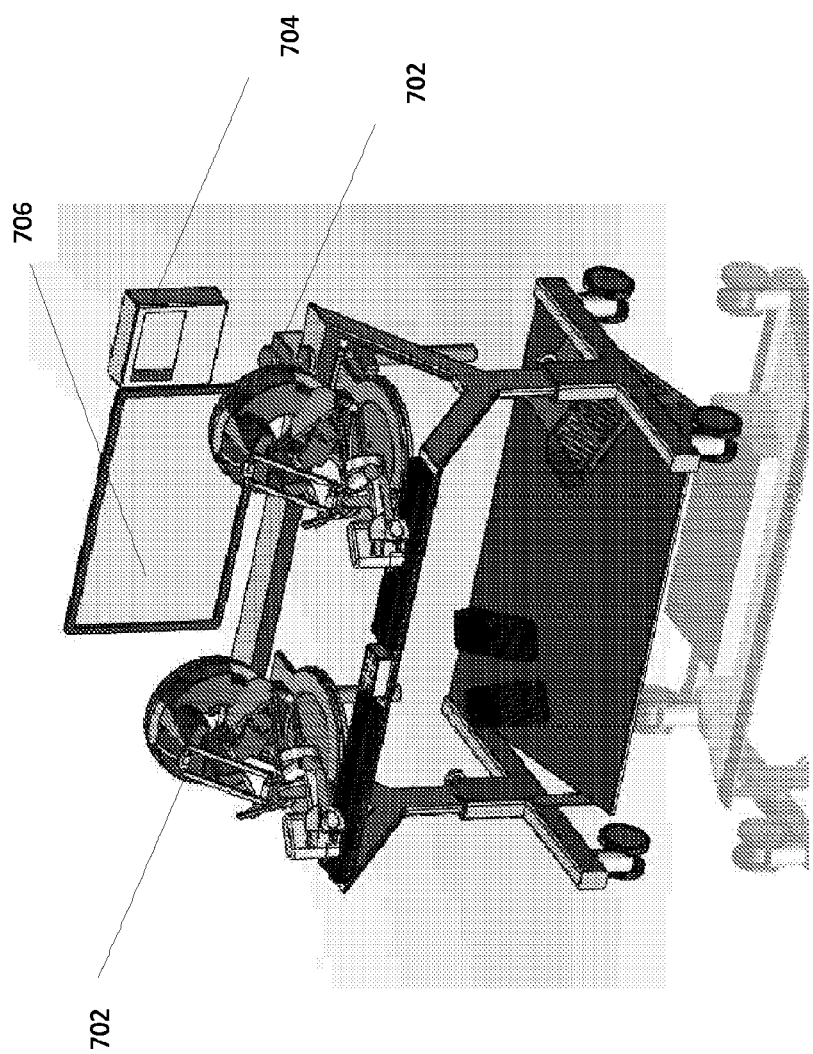
FIG. 7 shows a perspective view of the master section of the endoscopy system of FIG. 1 with position input devices (PID) and a display in accordance with the present embodiment.
Figure 8:
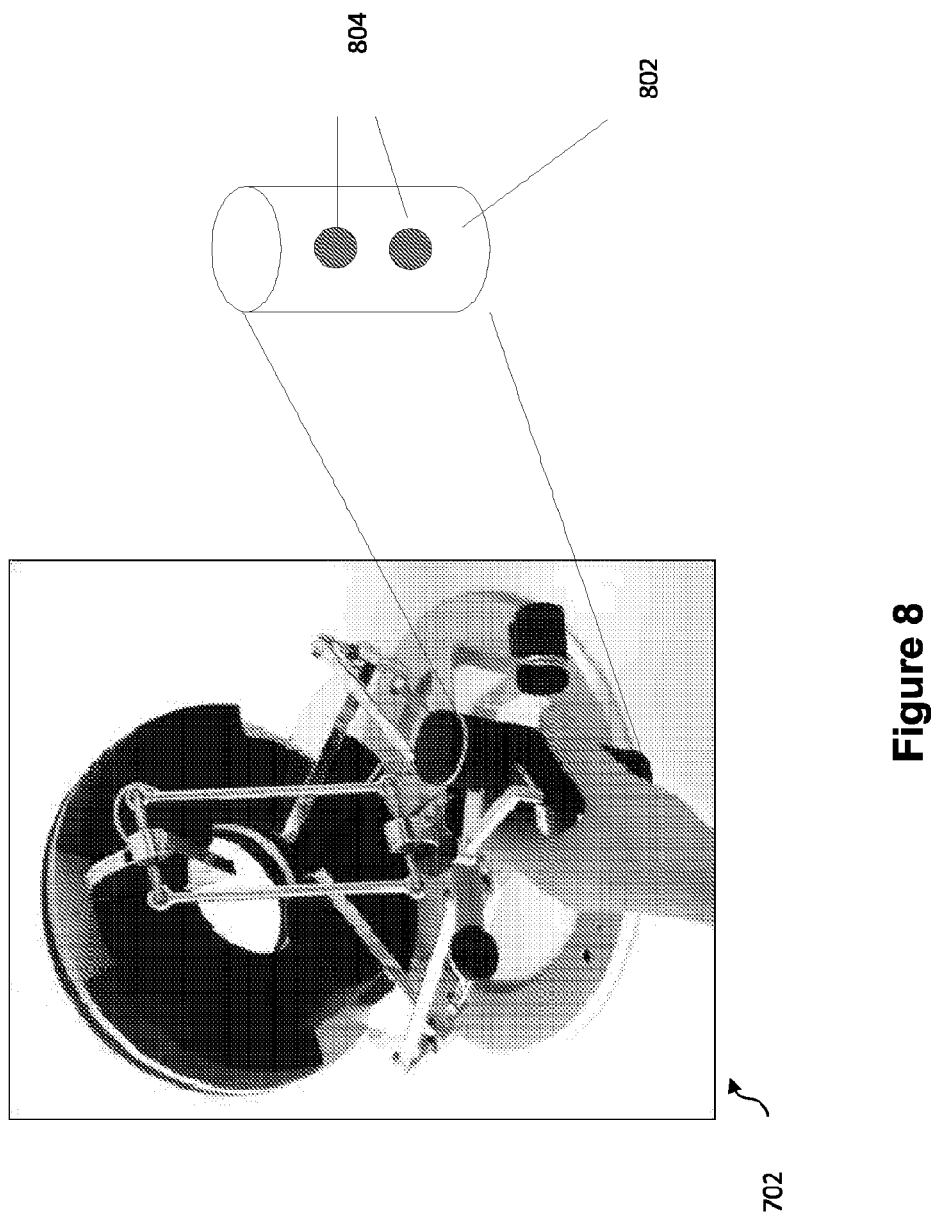
FIG. 8 shows an expanded view of one of the position input devices (PID) in accordance with the present embodiment.

From FIG. 7, it will be appreciated that the PIDs 702 are located at the master section 100 of the endoscopy system 10. The PID 702 allows movement control of the robotic members 410 and activation of air insufflation, water irrigation and fluid suction functions of the solenoid valves 360 (see FIG. 3) while air insufflation, water irrigation and fluid suction functions of the solenoid valves 360 can be also activated through buttons on the transport endoscope 320. With reference to FIG. 8, which provides an expanded view of one PID 702, each PID 702 has a handle 802 with two buttons 804. Each of three of the four buttons 804 is assigned to provide remote control of one of the air insufflation, water irrigation and fluid suction functions of the solenoid valves 360. The fourth button is to activate teleoperation of the robotic members 410. This is to make sure if the user intends to initiate teleoperation after the surgical instruments get initialized and calibrated and are ready to be remotely controlled through the PIDs 702. This teleoperation initiation command can be sent through another channel such as a foot pedal.

Before the three buttons 804 are able to control their respectively assigned air insufflation, water irrigation and fluid suction functions of the solenoid valves 360, the cart power switch 368 and the air/water power switch 370 have to be switched on, whereby pressing the buttons 804 will effect air insufflation, water irrigation and fluid suction. These are essential during surgery for purposes such as inflating the gastrointestinal tract, cleaning a camera lens inserted through the flexible elongate shaft of the transport endoscope 320 (or embedded on the distal end of the transport endoscope 320) and to remove unwanted fluid (such as from cleaning of the camera lens).

Figure 5:
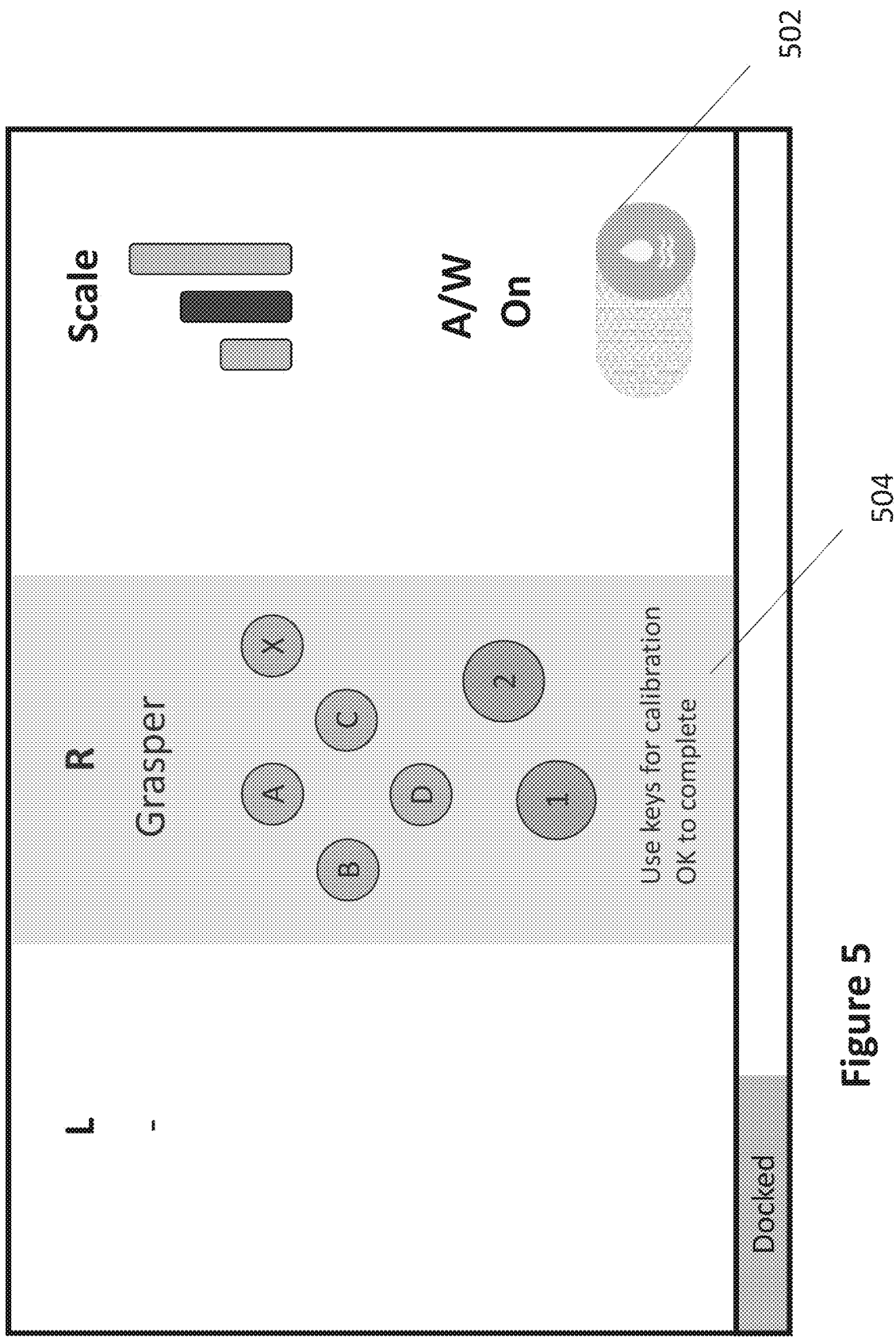
FIG. 5 shows an activation and/or calibration status of robotic members of the endoscopy system of FIG. 1 in accordance with the present embodiment.
Figure 6:
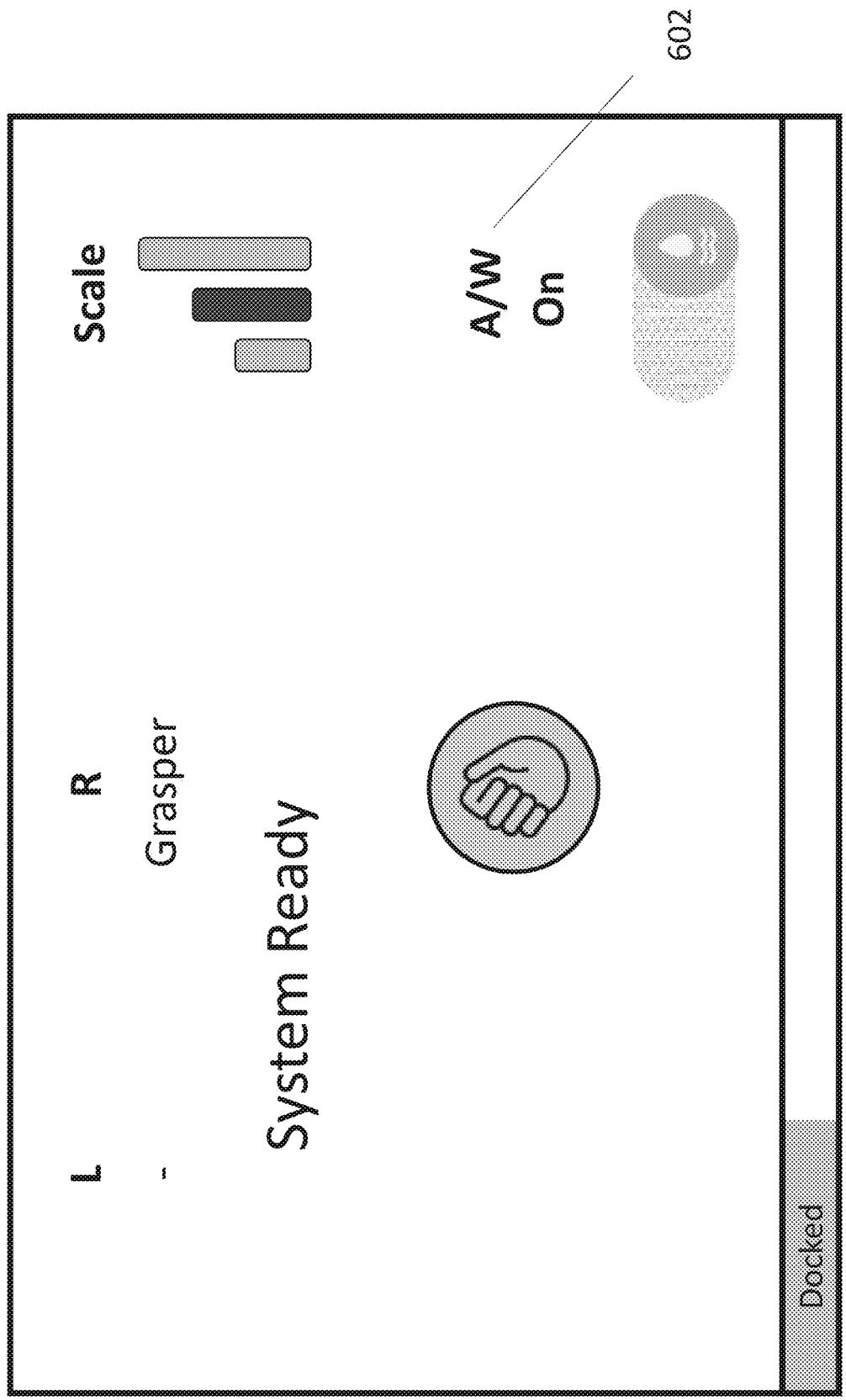
FIG. 6 shows a status of a remotely-controllable valve control box from a master section of the endoscopy system in accordance with the present embodiment.

The display 704 serves to show the activation status of the remotely-controllable valve box controller 348 from the PIDs 702; the calibration status of the robotic members 410 (see reference numeral 504 in FIG. 5); the activation status of the air insufflation, water irrigation and fluid suction functions commanded through buttons on the transport endoscope 320 and/or three buttons 804 on the PIDs 702. When the air/water power switch 370 is switched 'ON' and remote control of the valve controller box 348 is activated (see reference numeral 602 in FIG. 6 as displayed 'ON' in the display 704), the buttons 804 are activated to allow remote control of the solenoid valves 360. When the remote control of the valve controller box is deactivated, the display 704 will display the word 'OFF' to convey that the buttons 804 are deactivated. The display 704 will also update when the buttons 804 and/or buttons on the transport endoscope 320 are pressed and provide an indication as to which of the air insufflation, water irrigation and fluid suction functions are being operated at any point of time. Together with a main display 706 showing images of the air insufflation, water irrigation and fluid suction streamed by the camera lens inserted through the flexible elongate shaft of the transport endoscope 320, the display 704 provides an additional way for an operator to verify which of the air insufflation, water irrigation and fluid suction functions are being operated at any point of time. From FIGS. 4 to 8, it will be appreciated that the valve controller box 348 provides a means to integrate operation and monitoring of air insufflation, water irrigation and fluid suction functions.

FIG. 9A shows components of the docking station 500 to which a proximal end 920 of the transport endoscope 320 is attached.

Figure 14:
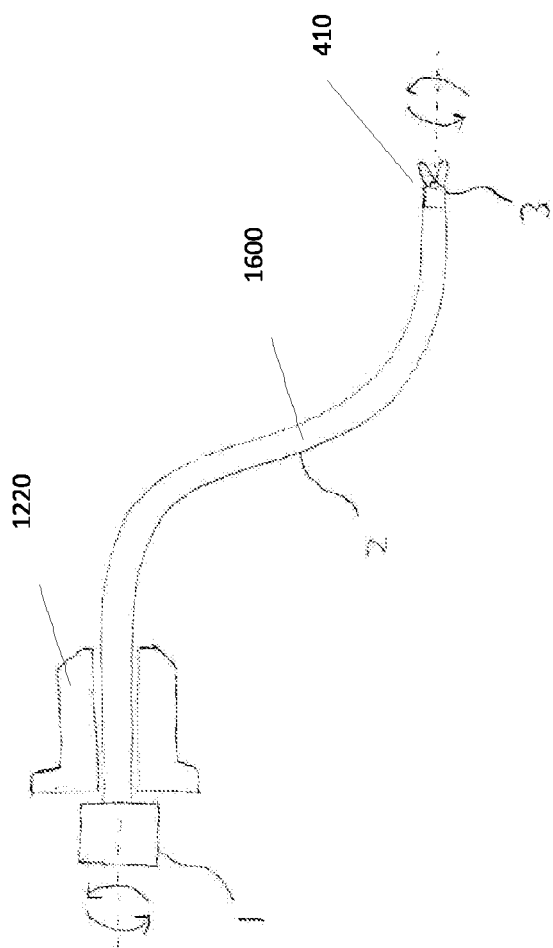
FIG. 14 shows a schematic of the flexible elongate member of the endoscopy system of FIG. 1 in accordance with the present embodiment.

The docking station 500 houses a motor box that contains actuators used to rotate the flexible elongate member 1600 coupled at its distal end to the robotic members 410 (confer FIG. 14). The actuators also articulate the robotic member 410 at the distal tip of the elongate member 1600. The motor box is located within a translatable housing 926 that comprises a stationary lower portion 930 onto which a movable upper portion 928 translates. The dimension of the movable upper portion 928 is larger than that of the stationary lower portion 930, so that the stationary lower portion 930 and the movable upper portion 928 have a telescopic structural arrangement in that a portion of the stationary lower portion 930 enters into or withdraws from the movable upper portion 928, depending on the direction of translation of the movable upper portion 928. The gap or free play between the stationary lower portion 930 and the movable upper portion 928 is adjusted such that foreign particles are prevented from entering into the motor box housed within the translatable housing 926, while fluid and particles that the motor box attracts from endoscopy operation is kept outside the translatable housing 926.

The movable upper portion 928 translates to allow the robotic members 410 to allow fine movement within the organism on the operating table 20.

When the movable upper portion 928 translates to push the flexible elongate member 1600 further into a snugly fitted lumen within the flexible elongate shaft of the transport endoscope 320, there is a tendency for the flexible elongate member 1600 to buckle as shown in the dotted portion of FIG. 9A. Further, the protective cover 1606 may be scraped off during the translation. In FIG. 9A, the buckling is minimized through the use of an anti-buckling tube 924 that the flexible elongate member 1600 enters downstream of the motor box towards the transport endoscope 320, specifically in the exposed portion between the actuators of the motor box and the proximate end 920 of the transport endoscope 320. This anti-buckling tube 924 thus acts as a guiding member between an actuator of the flexible elongate member 1600 and the transport endoscope 320. The anti-buckling tube 924 is held in place by a support 932 that extends from a portion of either a base 934 to which the transport endoscope 320 docks or stationary lower portion 930 of the translatable motor housing 926. In addition, the anti-buckling tube 924 is flared at both ends to facilitate straightening of the robotic members 410 during insertion and removal and to prevent damage to the protective cover 1606 by sharp features at the ends of the anti-buckling tube 924 during insertion and extraction of the elongate member 1600, which is undertaken for example at the end of a surgical procedure, or when switching to a new surgical instrument of a different function. The anti-buckling tube 924 may be realized using rigid structures, such as a pipe.

This buckling of the elongate member 1600 is further minimized through the implementations shown in FIGS. 9B, 10 and 11A, as further described below.

The first implementation of FIG. 9B further alleviates the above buckling and scrape off problems by having at least a portion 1420 of the shaft 1402 rigid, the portion 1420 being adjacent to where the flexible elongate member 1600 attaches to the adaptor 906.

Figure 10:
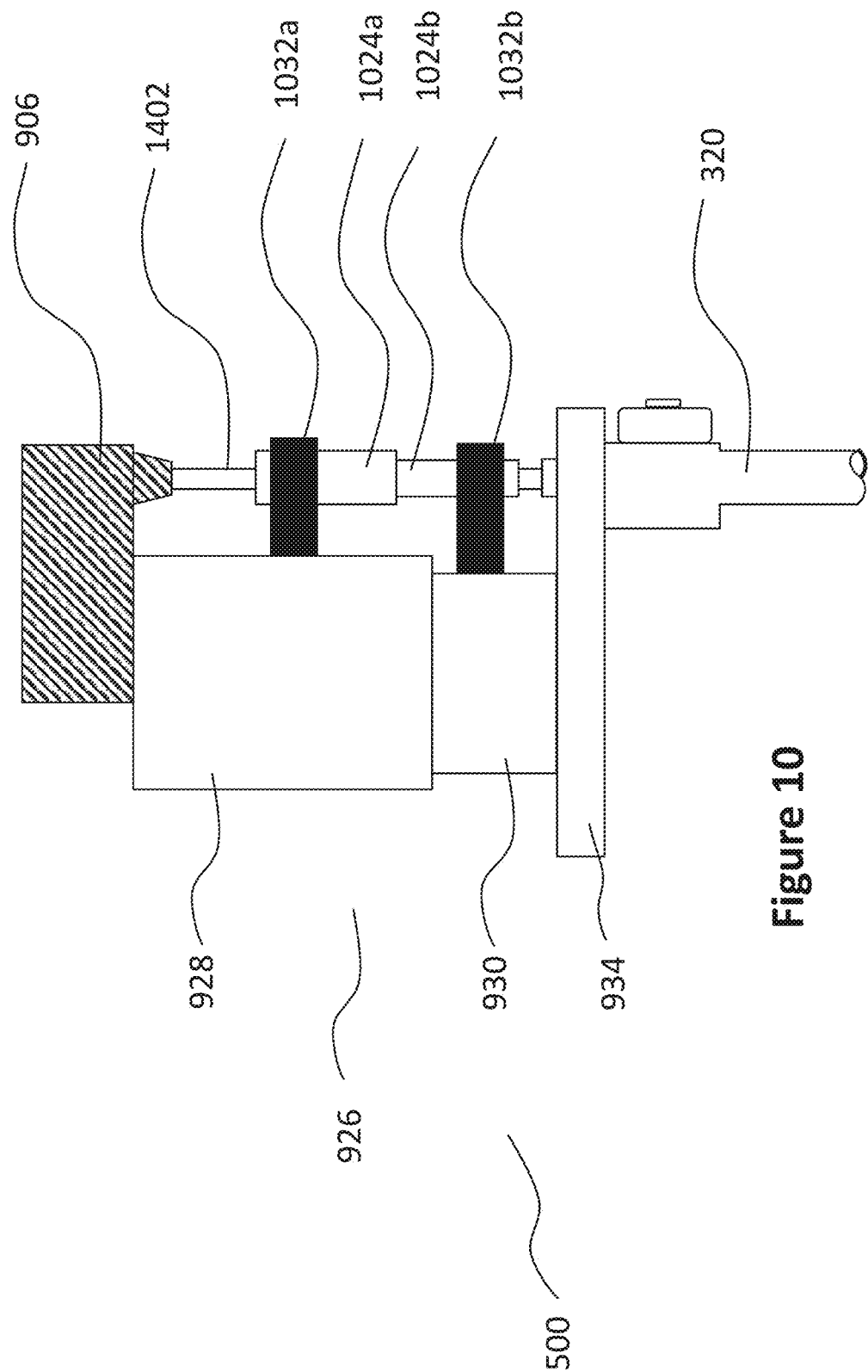
FIGS. 10 and 11A show schematic illustrations of the docking station of the endoscopy system of FIG. 1 in accordance with the present embodiment.
Figure 11A:
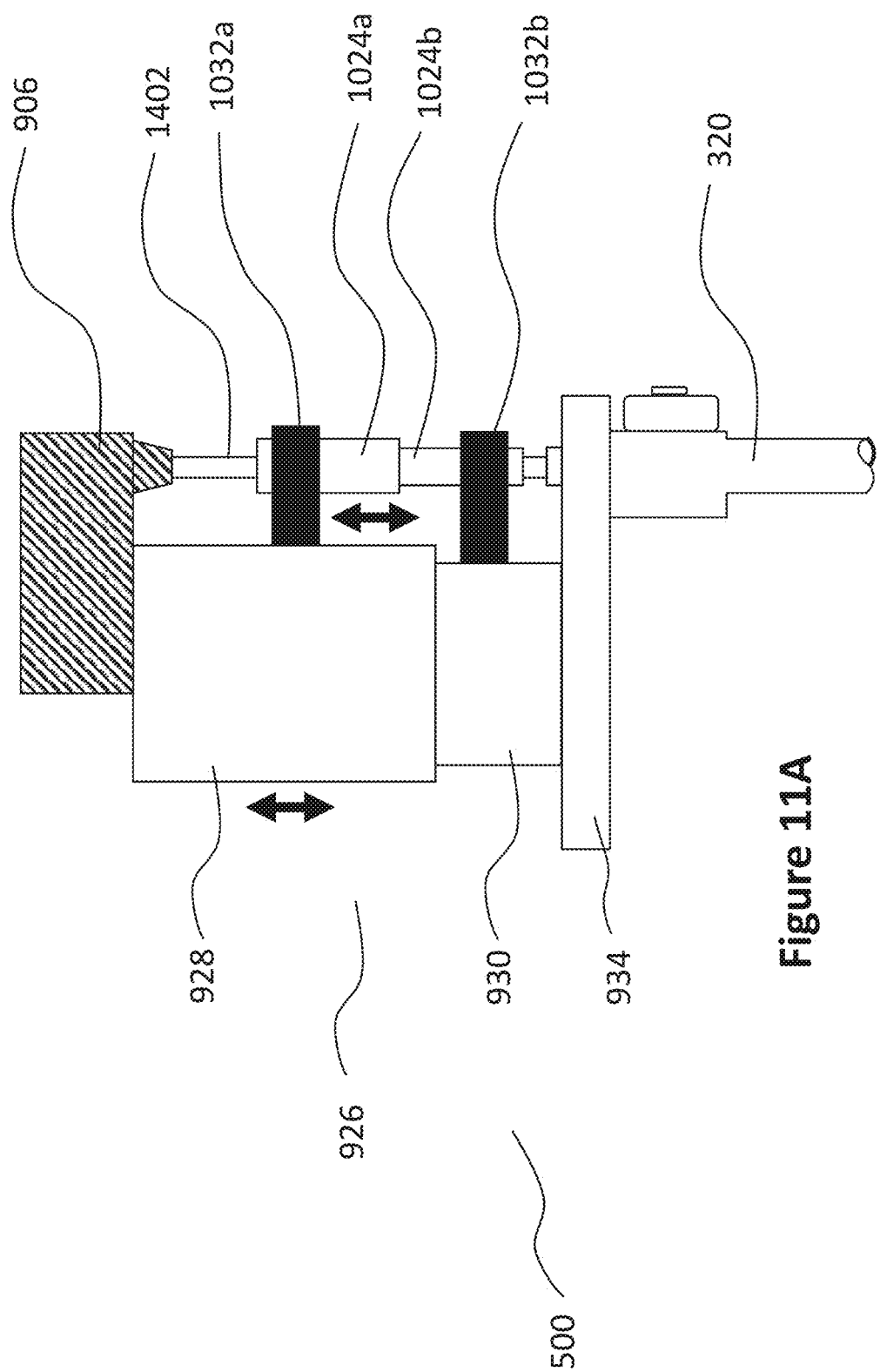

FIGS. 10 and 11A show a sketch of a second implementation of the docking station 500 to which a proximal end 920 of the transport endoscope 320 is attached, this second implementation seeking to alleviate the buckling of the flexible elongate member 1600 shown in FIG. 9A. FIG. 10 shows the movable upper portion 928 in a fully extended state, while FIG. 11A shows the movable upper portion 928 during translation.

While the first implementation uses a single anti-buckling tube 924, the second implementation uses two anti-buckling tubes 1024a and 1024b. The two anti-buckling tubes 1024a and 1024b have a telescopic structural arrangement in that one of the two anti-buckling tubes 1024a and 1024b has a larger dimension than the other, where when the movable upper portion 928 of the translatable housing 926 translates, the anti-buckling tube 1024a, 1024b with the smaller dimension enters into the anti-buckling tube 1024a, 1024b with the larger dimension. In FIGS. 10 and 11A, it is shown that the anti-buckling tube 1024a has a smaller dimension and acts as an inner guide, while the anti-buckling tube 1024b has a larger dimension and acts as an outer guide. However, it is also possible that the anti-buckling tube 1024a has a larger dimension, while the anti-buckling tube 1024b has a smaller dimension. It will be appreciated that in the second implementation of FIGS. 10 and 11A, it becomes optional to make a portion of the flexible elongate member 1600 rigid.

The anti-buckling tube 1024a is held in place by a support 1032a that protrudes from the movable upper portion 928, while the anti-buckling tube 1024b is held in place by a support 1032b that protrudes from a portion of either the base 934 to which the transport endoscope 320 docks or the stationary lower portion 930 of the translatable motor housing 926. When the movable upper portion 928 translates, the anti-buckling tube 1024a will also translate. By eliminating relative translation movement between the anti-buckling tube 1024b and the elongate member 1600, wearing down of the protective cover 1606 is reduced. Similar to the anti-buckling tube 924 of FIGS. 9A and 9B, the duo piece anti-buckling tube 1024a and 1024b is flared at its ends to facilitate removal of the robotic members 410. In both the first and second implementations, the singular anti-buckling tube 924 and the duo piece anti-buckling tube 1024a and 1024b is detachable from the docking station 500 for sterilization or for replacement with a new singular anti-buckling tube 924 and a new duo piece anti-buckling tube 1024a and 1024b.

FIGS. 9A, 9B, 10 and 11A show that the translatable housing 926 has a substantially vertical orientation, with the movable upper portion 928 undergoing vertical translation to move the flexible elongate member 1600. However, it will be appreciated that the translatable housing 926 may be placed in other orientations (not shown), such as a horizontal one, whereby the movable portion translates in a substantially horizontal manner, or an inclined one, whereby the movable portion moves along an inclined axis.

The anti-buckling tubes 1024a and 1024b can become soiled during use. Thus, it is advantageous that they be designed to be cleaned and sterilized in place or otherwise be removable for cleaning separately so that they can be reused. Alternatively, the anti-buckling tubes 1024a and 1024b may be designed for single-use and disposable, in which case a fresh tube is supplied for each procedure.

If the anti-buckling tubes 1024a and 1024b are designed to be reused, the material of the anti-buckling tubes 1024a and 1024*b* should be chosen to ensure compatibility with the prescribed cleaning and sterilization method. As a wide range of cleaning and sterilization solutions are in use in different regions of the world, a material with broad compatibility across multiple solutions is advantageous. As such, corrosion resistant metals such as stainless steels or corrosion resistant polymers are good material choices for the anti-buckling tubes 1024*a* and 1024*b*.

If the anti-buckling tubes 1024*a* and 1024*b* are designed for operable decoupling from the translatable motor housing 926 during cleaning and sterilization, an attachment means facilitating decoupling of the anti-buckling tubes 1024*a* and 1024*b* from the translatable motor housing 926 should also facilitate ease and thoroughness of cleaning and/or sterilization. Many possible cleanable attachment means are conceivable. For example, attachment means that use magnets are particularly advantageous as they can be embedded leaving a smooth, flat, or convex outer profile with few, if any, crevices to ease cleaning by brush or wipe down with a cloth. In one implementation, the supports 1032*a* and 1032*b* are manufactured using magnetic material or at least have embedded magnets, whereby the support 1032*a* is welded to the anti-buckling tube 1024*a* and the support 1032*b* is welded to the anti-buckling tube 1024*b*.

Figure 11B:
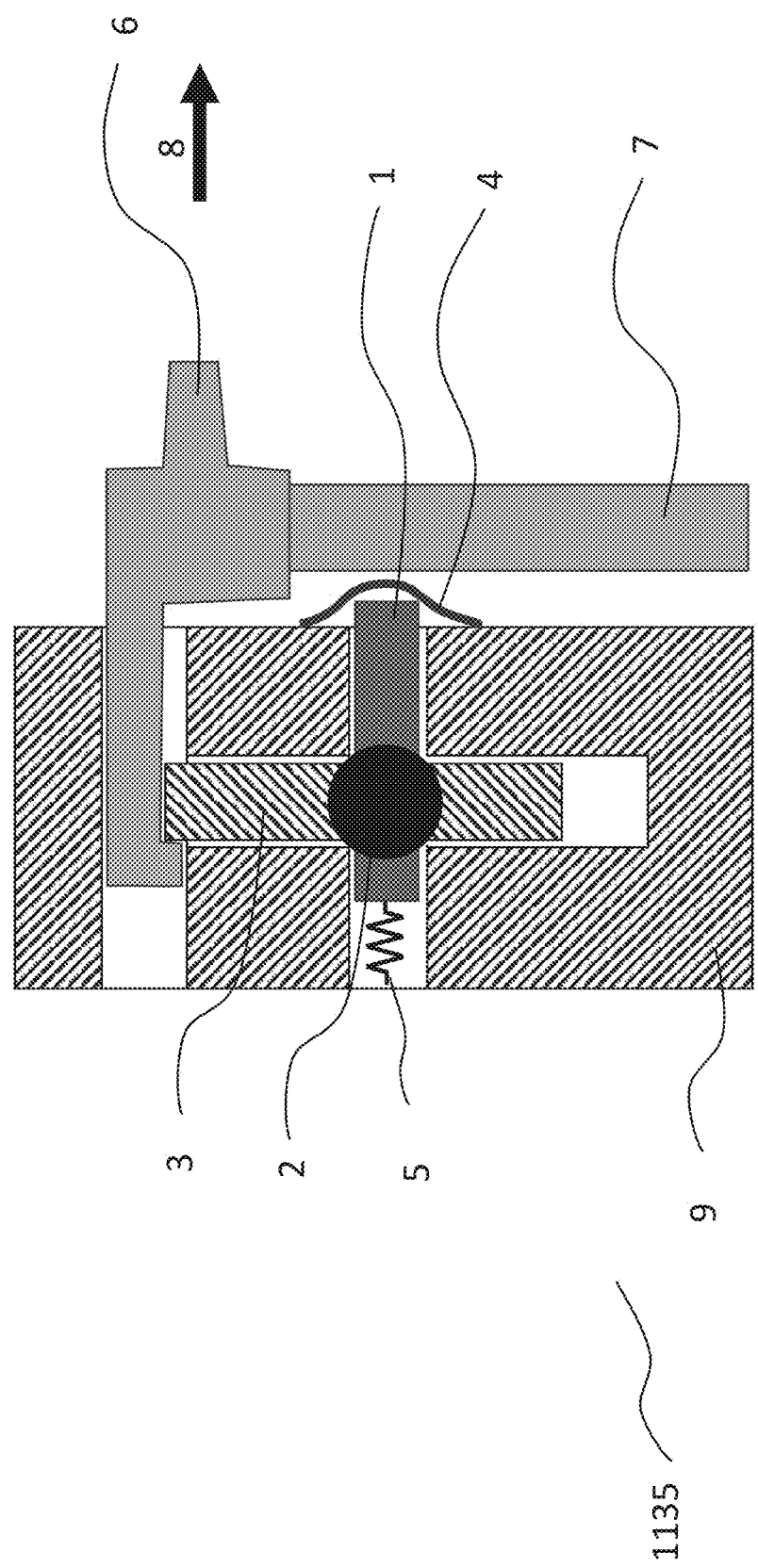
FIGS. 11B and 11C show structures used to realize components of the docking station of the endoscopy system of FIG. 1 in accordance with the present embodiment.
Figure 11C:
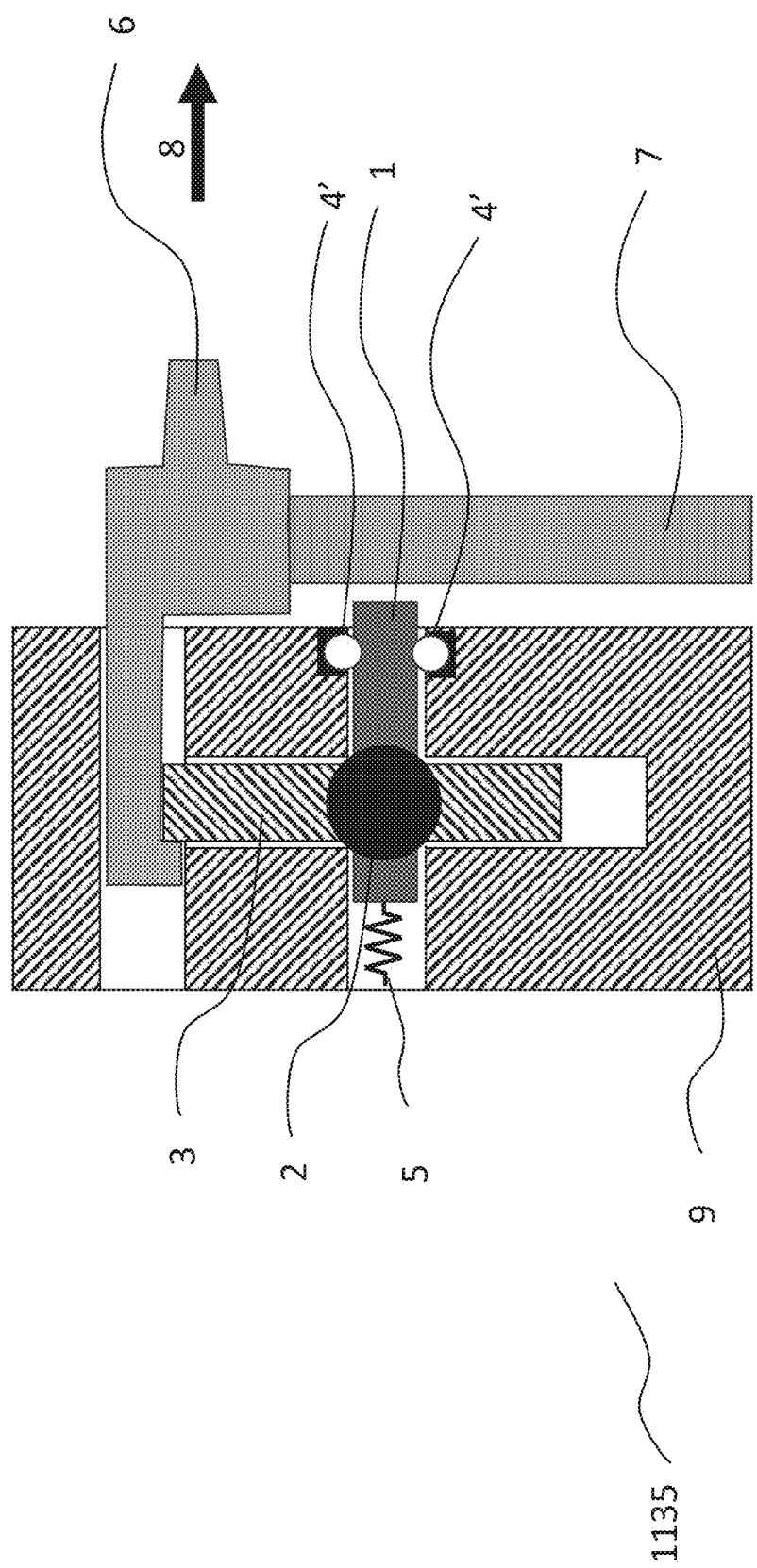

FIGS. 11B and 11C show structures that use non-magnetic means such as mechanical means to attach anti-buckling tubes to the translatable motor housing 926 of FIGS. 9A, 9B, 10 and 11. Non-magnetic means are employed in scenarios where magnets used in the supports 1032*a* and 1032*b* (see FIGS. 10 and 11A) may interfere with the operation of magnetic components within the translatable motor housing 926.

If magnetic attachment of the anti-buckling tubes 1024*a* and 1024*b* is not possible a dynamic-engagement mechanism 1135 shown in FIG. 11B may be used. The dynamic-engagement mechanism 1135 has a body 9 having a first opening to accommodate at least a portion of a handle 6 of the anti-buckling tube 7. The body 9 houses a mechanical catch arrangement that releases the anti-buckling tube 7 from the body 9 when the anti-buckling tube 7 is to be removed for cleaning. In the implementation shown in FIG. 11B, the mechanical catch arrangement comprises a rod 2, an abutment member 3, a release button 1 and a biasing structure 5. The rod 2 is pivotally connected to the abutment member 3 and the release button 1 and is disposed to move along a longitudinal section of the body 9. The body 9 has a second opening through which a portion of the release button 1 protrudes from the body 9; while a portion of the release button 1 that is within the body 9 is coupled to the biasing structure 5. A membrane/impermeable barrier 4 covers the portion of the release button 1 that protrudes from the body 9.

When the release button 1 is operated through the membrane/impermeable barrier 4, the abutment member 3 is mechanically activated in the direction shown in the arrow, whereby the rod 2 pulls the abutment member 3 downwards. The handle 6, which is welded to the anti-buckling tube 7, is released in the direction 8. The membrane/impermeable barrier 4 can be permanently attached to the body 9 or removable for cleaning and sterilization.

FIG. 11C shows a variant of the implementation shown in FIG. 11B. The dynamic-engagement mechanism 1135 of FIG. 11C is the same as the dynamic-engagement mechanism 1135 of FIG. 11B. However, instead of using a membrane/impermeable barrier 4, the body 9 of the dynamic-engagement mechanism 1135 of FIG. 11C uses a dynamic seal 4" to seal the body 9 from soiling. The dynamic seal 4" may be, for example, a washer where frictional engagement between the wall of the second opening of the body 9 through which the button 1 protrudes and a facing surface of the dynamic seal 4" hinders fluid from entering the body 9 internal cavity.

FIGS. 11D to 11G depict yet another variant of the couple of the anti-buckling tubes 1340 to the anti-buckling tube holder 1342 which can be achieved through mechanical means using non-permanent plastic deformation properties of the anti-buckling tube 1340. The anti-buckling tube 1340 comprises a portion of compliance feature/geometry 1344 which can temporarily deform to be fitted into the rigid portion of the anti-buckling tube holder 1342. The anti-buckling tube 1340 can either be attached/detached to the anti-buckling tube holder 1342 in a perpendicular direction to the motor housing face 1350 or the angle of attachment 1349 can be at an acute angle to the motor housing face 1350. In addition, three or more sided faces 1346 on the compliance feature/geometry 1344 enables a central plane 1348 of the anti-buckling tube 1340 to always be perpendicular to the motor housing face 1350. This allows the flexible elongate member to be inserted through the anti-buckling tube 1340.

Figures 12A, 12B:
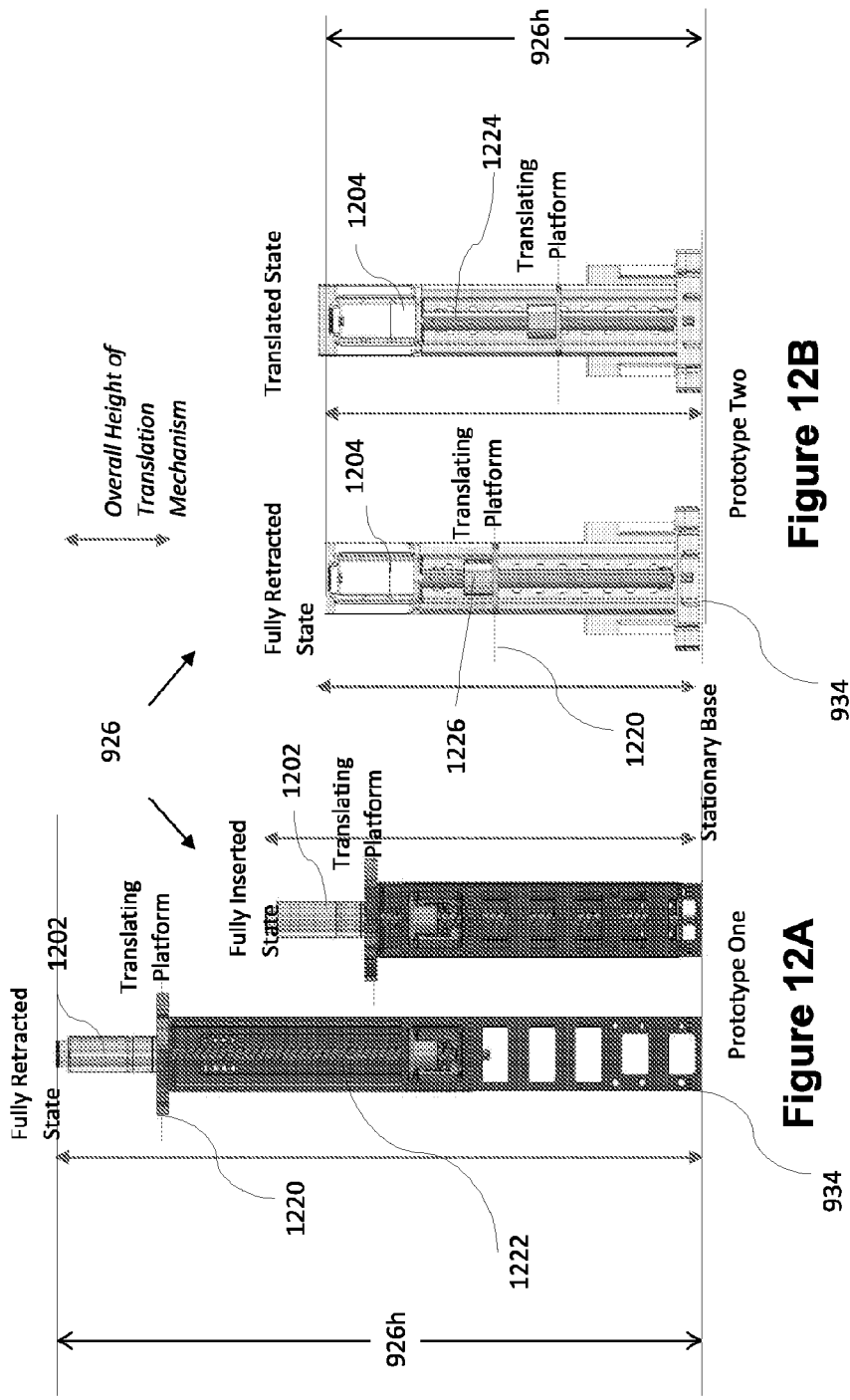
FIG. 12A shows a side view of a first implementation of a translation mechanism within a translatable housing of FIGS. 9A, 9B, 10 and 11A in accordance with the present embodiment.
FIG. 12B shows a side view of a second implementation of the translation mechanism within the translatable housing of FIGS. 9A, 9B, 10 and 11A in accordance with the present embodiment.

FIG. 12A shows a first implementation of the translation mechanism within the translatable housing 926 of FIGS. 9A, 9B, 10 11A and 11B, while FIG. 12B shows a second implementation of the translation mechanism within the translatable housing 926 of FIGS. 9A, 9B, 10 11A and 11B. In both FIGS. 12A and 12B, the housing is not shown. The translation mechanism of the translatable housing 926 comprises a motor (denoted using reference numeral 1202 in FIG. 12A and reference numeral 1204 in FIG. 12B) and a lead screw mechanism or ball screw mechanism (denoted using reference numeral 1222 in FIG. 12A and reference numeral 1224 in FIG. 12B). The overall height 926*h* of the translatable housing 926 is affected by the configuration of the translation mechanism (which comprises a motor and lead screw mechanism or ball screw mechanism) of the translatable housing 926 as explained below.

In FIG. 12A, the motor 1202 that drives the translation motion is mounted on the platform 1220 and translates together with the platform 1220. As the platform 1220 translates, the height 926*h* of the translatable housing 926 varies between the fully retracted state and the fully inserted state of the lead screw mechanism 1222.

A low height 926*h* is desirable because it eases docking of the drive mechanism of the robotic members 410 on the platform 1220. A portion of the drive mechanism, namely an instrument adaptor (which contains drums around which the cable pair shown in FIGS. 16, 17 and 18 wind at the proximate end), is shown in FIGS. 9A, 9B and 10 and denoted using the reference numeral 906.

In the configuration of FIG. 12B, the translation motor 1204 that translates the platform 1220 is mounted onto a stationary bracket. The platform 1220 (on which the housing of the movable upper portion 928 is placed) is allowed to translate by being mounted to a member 1226 that is rotatably coupled to the lead screw mechanism 1224 driven by the translation motor 1204. This member 1226 may be an object with a hole, such as a nut.

For the same range of translation motion, the height 926*h* of the translatable housing 926 of FIG. 12B will be lower than that of FIG. 12A as the screw mechanism 1224 of FIG. 12B does not translate, whereas the screw mechanism 1222 of the motor 1202 of FIG. 12A translates while it is being driven by the motor 1202.

There are crevices between the output shaft chassis 1304 and a motor output shaft 1302. If there is fluid ingress into such a crevice, it would pose a risk or a malfunction to the fluid sensitive components around the output shaft 1302.

A shield 1306 is fitted around the output shaft 1302 between the fluid sensitive components and an internal wall of the output shaft chassis 1304. This shield repels fluid that ingresses into the crevices and thus prevents the ingressed fluid from coming into contact with the fluid sensitive components. The shield 1306 is particularly advantageous over using a shaft seal to prevent such fluid ingress, whereby use of the shaft seal around the output shaft 1302 introduces friction to the shaft rotation.

Figure 13:
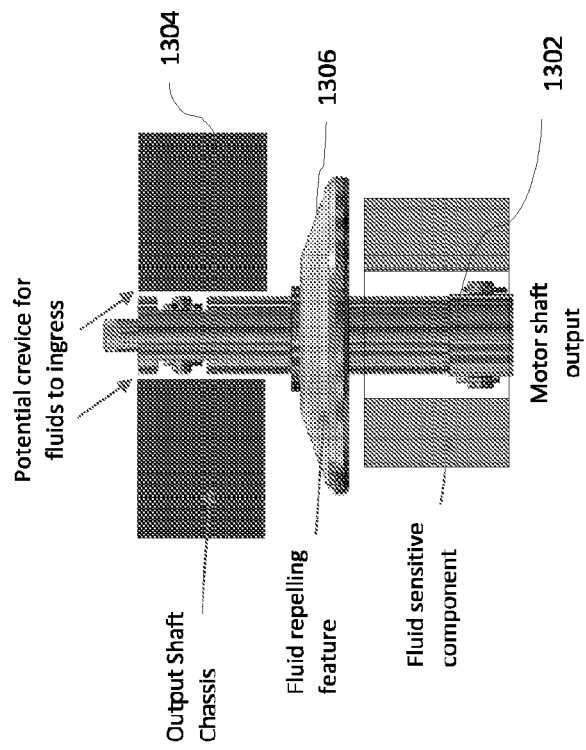
FIG. 13 shows a side view of a motor box to control a joint of a flexible elongate member of the endoscopy system of FIG. 1 in accordance with the present embodiment.

FIG. 14 shows a schematic of a flexible elongate member 1600 that is coupled at its distal end to the robotic member 410 and at its proximal end to a drive mechanism. The drive mechanism consists of a series of mechanical linkages that transmit motion from actuators to the adaptor 906 (FIGS. 9A and 9B). The adaptor 906 contain motivators, for example one or more drums, around which a cable pair winds that allow movement control of the robotic members 410, the cable pair running within the flexible elongate member 1600. In one implementation, a motor box containing one motor shaft (see reference numeral 1302 of FIG. 13) is used to rotate the flexible elongate member 1600 to which the robotic members 410 are connected.

As the flexible elongate member 1600 has to effectively propagate actuation that is applied at its proximal end to the distal end (such as rotation or a translation), a part of it, shaft 1402, may be realized using a rotational-motion transmitting device, such as a torque coil, that possesses low rotational backlash, good torque transmission, and low compressibility. The rotational-motion transmitting device also must be flexible enough to conform to the transport endoscope 320. To achieve this mix of properties, the rotational-motion transmitting device used for the shaft 1402 is designed to incorporate one or more of the following features.

A first feature uses a flat coil, of which one segment 1502 is shown in FIG. 15. From the cross-section view, the longer portion W of the coil is lain such that when the flat coil is wound edge to edge, it forms the longitudinal length of the shaft 1402. Example cross section dimensions for the flat coil is a width W of 0.2-0.4 mm and a thickness T of 0.05-0.15 mm. Contact between adjacent coils in the longitudinal direction transmit compressional forces with low backlash. Also, thinner layers enable the luminal space to be larger for a given outside diameter constraint, thus flat wire coils are preferable to round wire coils for a given number of layers within the coil.

A second feature uses multiple layers of a flat coil manufactured in accordance with the first feature. The direction of winding alternates between layers, which makes the resulting shaft 402 deliver 1 to 1 torque with less backlash. For example, the section cutout 1504 shown in FIG. 15 has three layers 4, 5 and 6. The inner layer 4 and the outer layer 6 are wound in the same direction, e.g., S rotation also known as left hand winding direction, while the middle layer 5 is wound in the other direction, the Z rotation also known as right hand winding direction. Each layer consists of 8-12 strands of flat wire wound in a helix, which results in the outside diameter of the coil ranging from 3 mm to 6 mm.

Alternating the direction of winding between layers results in 1 to 1 rotation between the proximal and distal ends with low backlash in the following way. When transmitting torque in a given direction, the left-hand wound coil or coils will introduce rotational backlash by expanding their diameter. Under the same direction of twist, right hand wound coil or coils will introduce rotational backlash by reducing their diameter. When coils of alternating wind directions are layered inside of each other, this source of rotational backlash is prevented. In the example above, the radial expansion of the left-hand wound coil is counteracted by the radial compression of the right-hand wound coil in the next outer layer. A minimum of three layers of alternating wind direction coils is required to eliminate this source of rotational backlash in both directions.

FIG. 16 shows a cross section view of a segment of a circular coil sheath, in accordance with a known implementation, where the circular coil sheath has a circular wire coil 1602 with a cable 1604 running through its lumen. Such circular wire coil sheaths are used to transmit compressive forces. The cable 1604 running inside the wire coil 1602 lumen provides tensile force in an action reaction pair. Low friction between these two components is desirable to prevent transmission loss of the tensile force. In the case of conduits that impose a high amount of bending on the wire coil 1602 sheaths, even small compressive forces applied to the wire coil 1602 sheath will cause it to buckle/kink, resulting in a narrowing of the lumen of the wire coil sheath. The narrowing of the lumen due to the buckling/kinking of the wire coil sheath results in increased friction with the cable 1604, reducing the force transmission efficiency of the cable 1604.

Figure 16A:
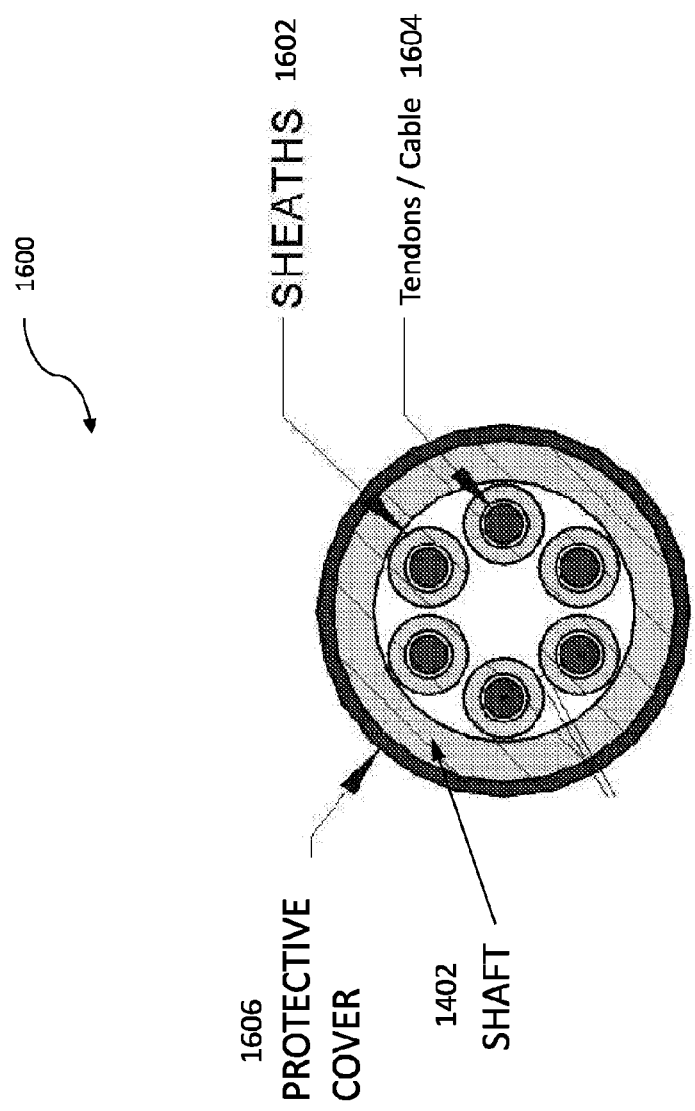
FIG. 16a shows a detailed cross section view of the flexible elongate member in accordance with the present embodiment.

FIG. 16a shows a detailed cross section view of a flexible elongate member 1600 (as shown in FIG. 14) including a protective cover 1606, a shaft 1402, a number of circular coil sheaths 1602 and cable 1604 contained within each circular coil sheath 1602.

For simplicity, only four pitches of wire coil 1a-1d are shown in FIG. 16. The compressive forces 4a, 4b on 1b come from adjacent pitches 1a and 1c. When the circular coil sheath is bent, this compressive force has an upward component. There is a counteracting downward force 5 from the tendency of the wire coil 1602 to retain its original shape. There is also a small downward force 6 exerted by the cable 1604 on 1b. However, when the compressive force from 4a, 4b is great enough, the circular surfaces where 1b interfaces with 1a and 1c form an unstable equilibrium whereby an incremental slip of 1b in the upward direction causes the angle of contact between adjacent pitches to change markedly. This in turn leads the direction of the compressive reaction forces 4a, 4b between adjacent pitches to change markedly. This in turn causes even more upward lateral slip of 1b in a virtuous cycle and leads to permanent deformation of the coil, known as buckling/kinking. This instability can propagate along the length of a sheath, as shown in FIG. 18.

FIG. 17 shows a cross section view of a segment of a rectangular wire coil sheath, in accordance with an improvement over the circular coil sheath of FIG. 16. The rectangular wire coil sheath has a wire coil 1702 with a substantially rectangular cross section. Similar to the circular coil sheath of FIG. 16, a cable 1604 runs through the lumen of the rectangular coil sheath of FIG. 17.

The improvement over FIG. 16 is that instead of a coil wire with a circular cross section, a coil wire 1702 with a rectangular cross section is used. When it is wound into a sheath, each pitch of the sheath has more stable contact with the adjacent pitches, such that external bending and compressive forces on the wire coil are less likely to cause the alternating pitches to slip in the lateral direction. The rectangular cross section is shorter in the direction of the wire coil sheath. This increases the pitch density, which results in a smaller amount of bending per pitch and hence an induced strain in the cross-section due to bending that is lower than induced strain of a lower pitch density coil under the same radius of bend. If the induced strain from bending and compressional forces is kept below the yield strain for the material, there will be no permanent buckling/kinking of the wire coil 1702. A slight movement upwards of coil 3*b* does not change the angle of attack of the compressive force from coils 3*a* and 3*c*. With a smaller pitch, the change in angle of attack is further reduced, leading to better anti-buckling performance than circular wire coil 1 while retaining the same bending properties.

A particular embodiment of the rectangular coil sheath is when the cross section has equal dimensions, i.e. it is a square coil sheath. This does not provide the benefits of increased pitch density, but still provides more stability against buckling because the angle of attack of the compressive force from coils 3*a* and 3*c* on 3*b* does not change with lateral deflection. Also, a square cross section coil has a greater cross-sectional area than the circular cross-sectional area of a circular wire coil of equivalent pitch. This makes it more resistant to lateral shear forces.

FIG. 18 shows a similar cross section view of the segment of the circular coiled wire sheath of FIG. 16. In this figure, the coiled wire sheath 1802 is made of a super-elastic material. One example of a super-elastic material is nitinol, an alloy of Nickel and Titanium. Nitinol has unique material properties in that it can be deformed to a large extent by loading but is still able to recover its original shape after the load is removed. In FIG. 18, a nitinol circular coiled wire sheath 1802 is highly compressed during periods of high loads on the cable 1604, and thus it undergoes temporary buckling. This increases the friction on cable 1604 (as shown in FIG. 16 and FIG. 16*a*), and reduces efficiency. After the coiled wire 1802 is unloaded/unbent, the coiled wire 1802 reverts to its original shape instead of remaining in the plastically deformed irregular shape. Hence, the coiled wire sheath 1802 may be operating at maximum efficiency for most of the time, without a degradation of efficiency over time.

Figure 19:
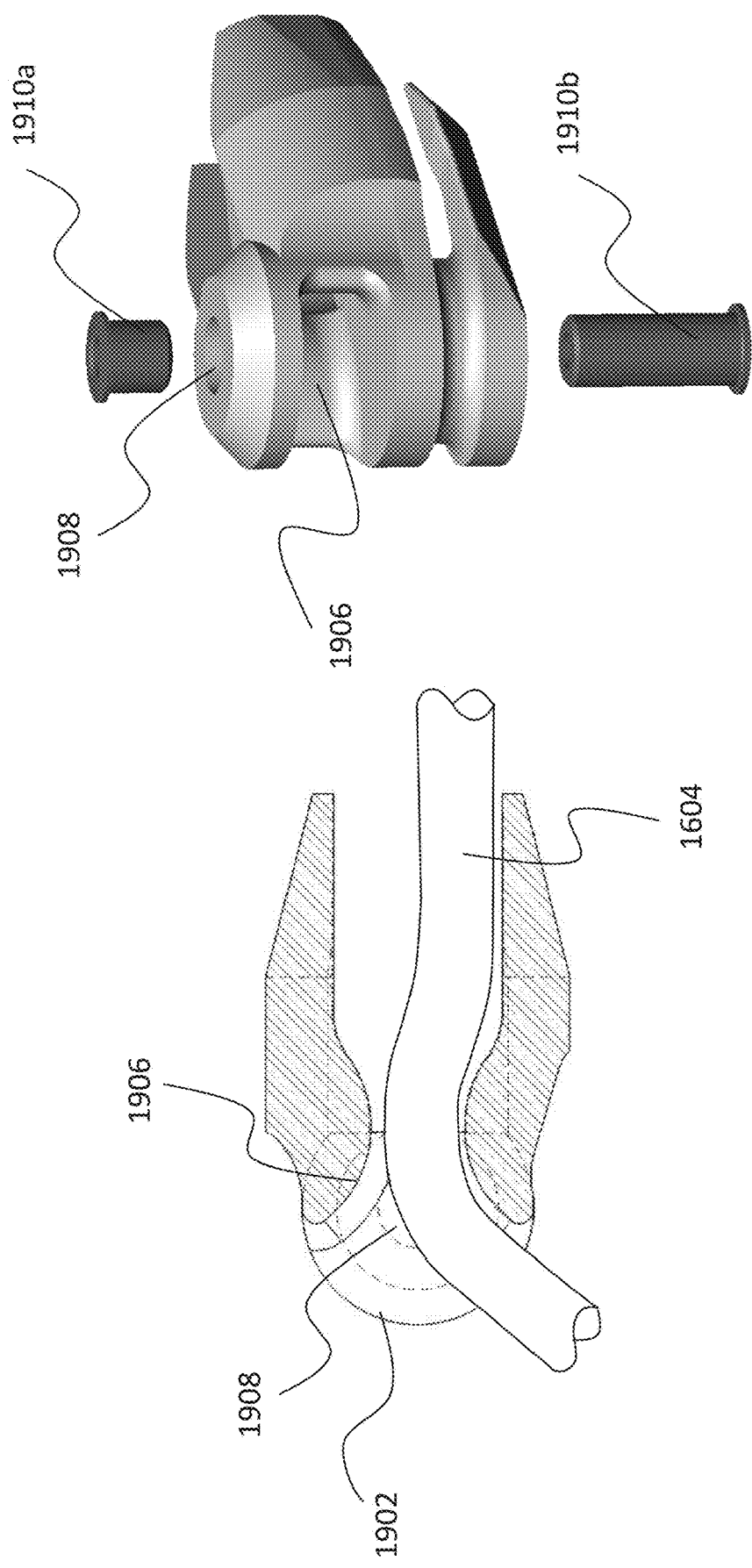
FIG. 19 shows a schematic diagram of an anti-kink support for electrical wires of the endoscopy system in accordance with the present embodiment.

FIG. 19 shows a schematic diagram of an anti-kink support 1902 for electrical wires. The anti-kink support may be located at a robotic member 410 and may increase the kink resistance of the wire 1604 (see FIGS. 14 and 16*a*) without affecting the function of a rotational joint. It can be appreciated that, in addition to the tendons/cable 1604, the shaft also carries electrical wires (not shown in FIG. 16*a* for the sake of simplicity), As shown in the FIG. 19, the anti-kink support 1902 of the current invention enforces a minimum bend radius on the wire 1604 by having curved inlets 1906. The minimum bend radius is determined experimentally such that wire does not experience bending fatigue failures within the expected life of the device, while minimizing the space required inside the device to accommodate the wire bending. The anti-kink support 1902 includes supports 1908 that allow it to pivot freely on pins 1910*a* and 1910*b* or similar non-pin shaped structure. This may allow the wire 1604 to achieve its energetically most stable state, i.e. possessing the lowest amount of total bending. The axis of rotation of the anti-kink support 1902 may be substantially co-located with the axis of articulation of the robotic member 410, such that the wire does not experience appreciable stretch or compressional forces throughout the articulation range of motion of the robotic member 410.

Figure 20A:
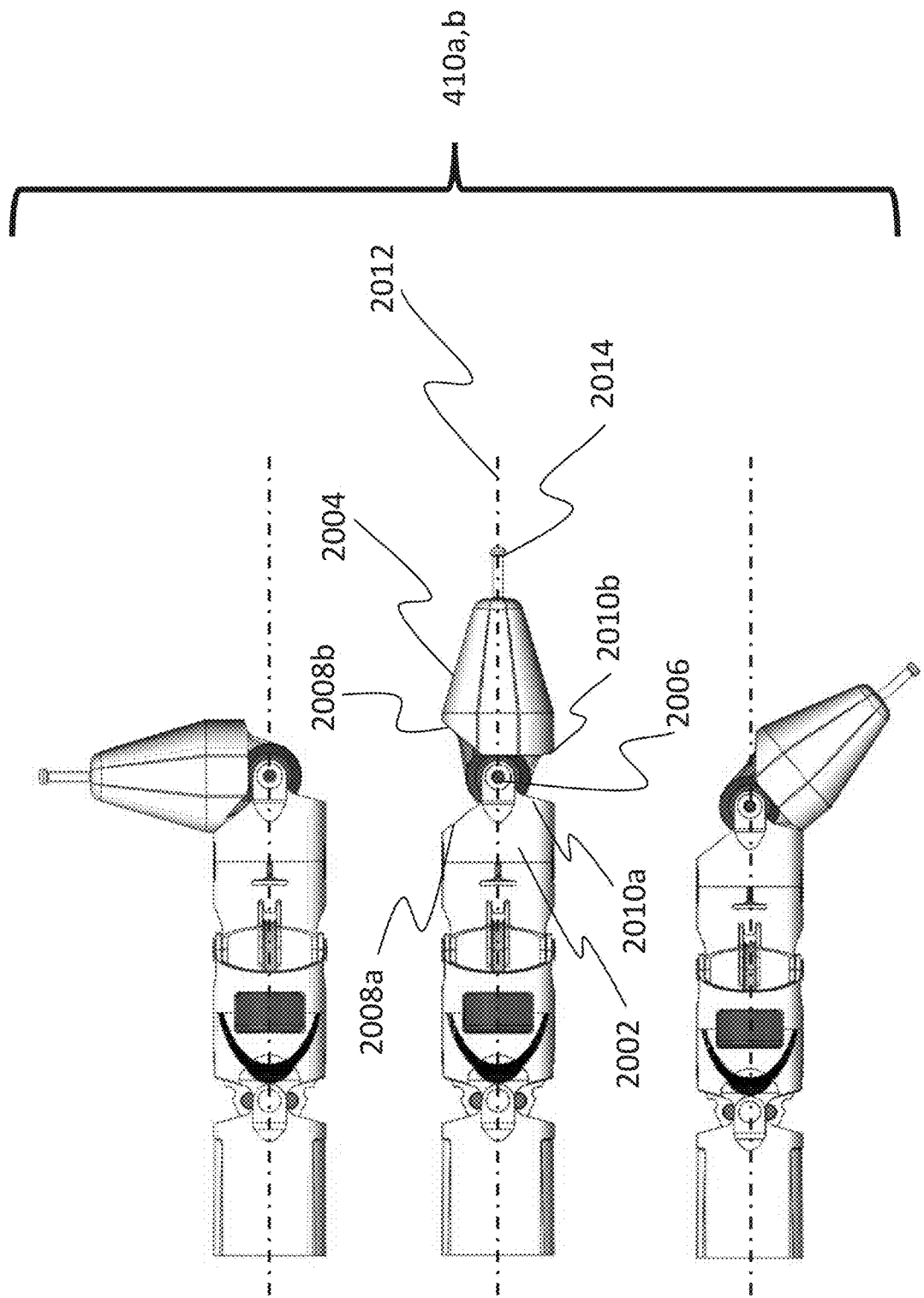
FIGS. 20a and 20b show close-up cross-sectional views of one of the robotic members of the endoscopy system in accordance with the present embodiment.

FIG. 20*a* shows a close-up cross-sectional view of one of the robotic members 410 according to an example embodiment. The robotic member 410 may have asymmetric ranges of motion such that there is enhanced visibility by the camera, which may lead to safer operation of the instrument. The joints 2006 of the robotic member 410 are allowed to move in a smaller angle in the direction away from the camera axis than in the direction towards the camera axis through the use of mechanical hardstops 2008*a*, 2008*b*, 2010*a*, 2010*b*. Alternative embodiments may involve the use of software and position sensing to achieve the same effect.

In an example embodiment, the robotic member 410 of FIG. 20*a* is shown with three stages of articulation, i.e. at neutral position (0°), 90° anticlockwise of the neutral position and 45° clockwise of neutral position. The base joint 2002 is fixed and is parallel to the axis of reference 2012. The distal joint 2004 rotates about the hinge 2006. The upper hardstops 2008*a* and 2008*b* provide the maximum degree of upward rotation allowed. In an example embodiment as shown, a maximum of 90° anticlockwise rotation about the neutral position is permitted. The surface of lower hardstops 2010*a* and 2010*b* may have a different angle as compared to surfaces of hardstops 2008*a* and 2008*b* such that the maximum degree of downward rotation is limited. In an example embodiment as shown, a maximum of 45° clockwise rotation about the neutral position is permitted. The cumulative effect of the asymmetry across multiple joints may determine the workspace at the distal end of the robotic member 410. The asymmetries among the joints can be optimized to provide maximum visibility of the distal end effector 2014.

Figure 20B:
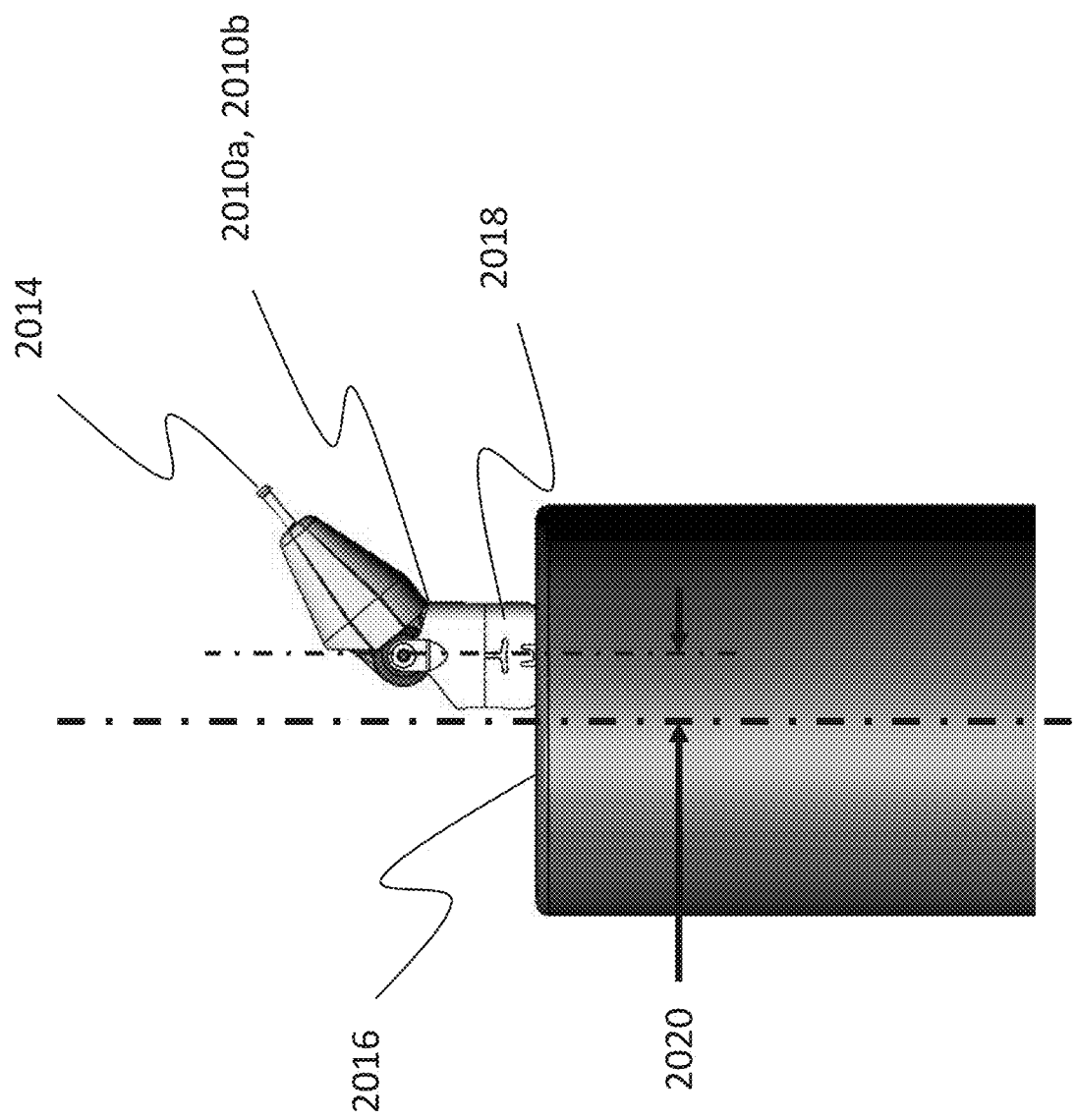

In an example embodiment, an implementation of the above concept is shown in FIG. 20*b* in conjunction with a camera 2016 adjacent to a robotic member 410. The robotic member 410 lies substantially parallel to the viewing direction of the camera, but with a small lateral offset 2020. When the robotic member 410 is articulated away from the camera 2016, the mechanical hardstops 2010*a*, 2010*b* limit the motion of the distal end effector 2014 from going too far out of the visual range.

The endoscopy system may include a torque joint located at the robotic instrument that makes use of a centrally aligned pulley with space saving sheet metal structural components and which does not use a central pin. Such a torque joint occupies as little cross-sectional space as possible yet provides the maximal amount of torque for a given cable force by centrally aligning the pulley so that the pulley's diameter may be maximized for a given diameter of the robotic member 410. Further, the torque joint allows pass-through elements to be routed without obstruction along both sides of the pulley. Using sheet metal to mount the centrally aligned pulley and transmit its torsional forces to the rest of the torque joint may allow thinner walls compared with other mounting solutions for a comparable manufacturing cost and hence a more compact pulley structure can be obtained. As the pulley is no longer directly connected to the hinge joints, a locating pin may be used temporarily during assembly to maintain a good alignment between the rotational axis of the pulley and the rotational axis of the torque joint.

Figure 21D:
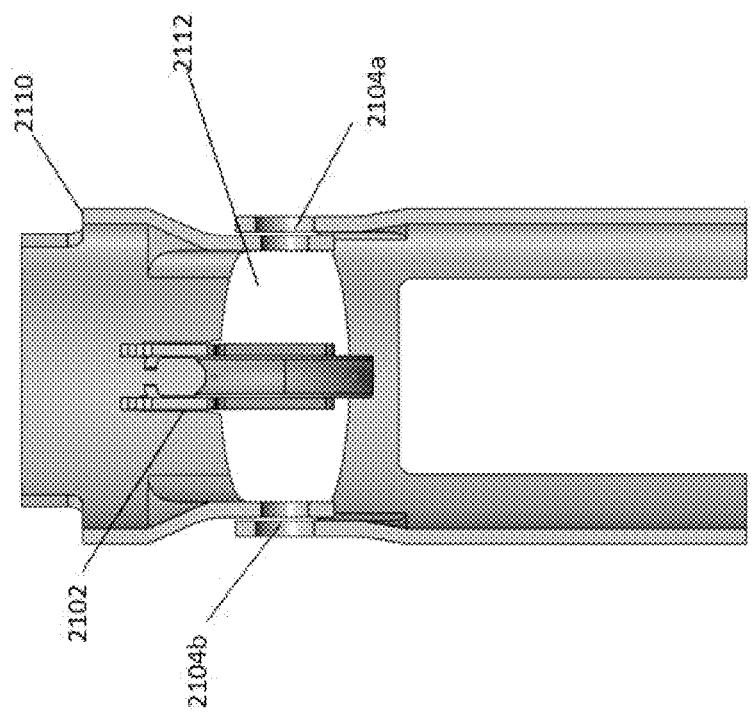
FIGS. 21c and 21d show cross sections of the torque joint with the pulley in accordance with the present embodiment.
Figure 21C:
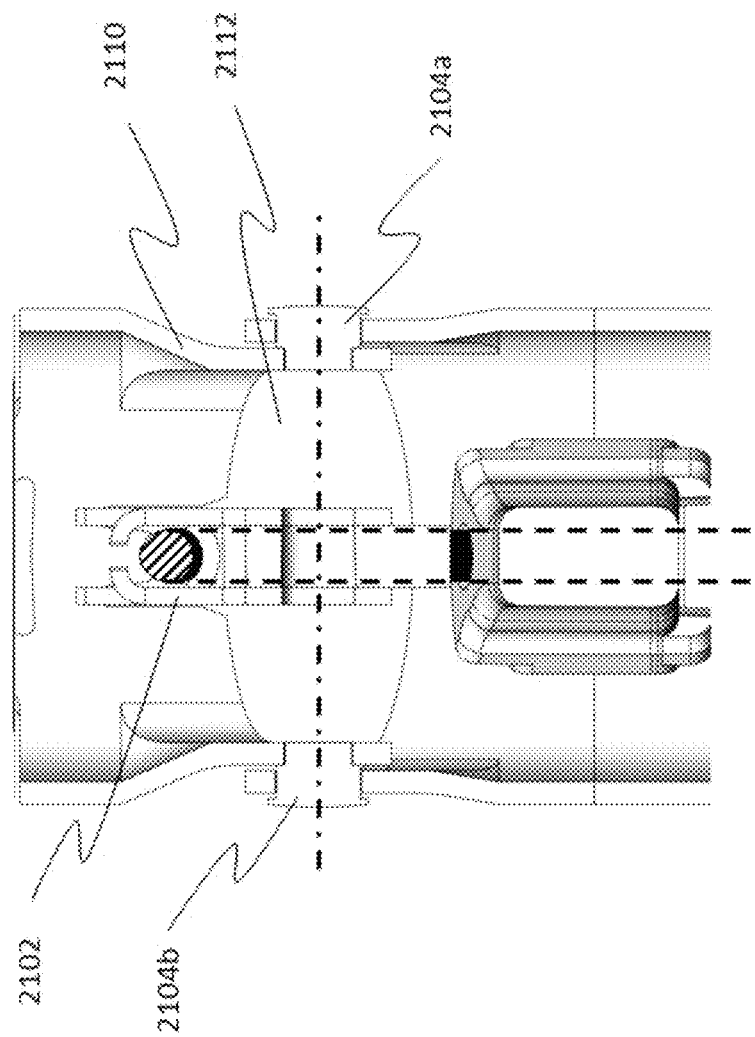

FIG. 21*a* shows a side view of a pulley 2102 while FIG. 21*b* shows a perspective view of the torque joint with the pulley 2102. The pulley 2102 may include triangular sheet metal mounting brackets 2116*a* and 2116*b*. The pulley 2102 may also contain features 2118*a*-2118*d* that assist in retaining the pulley wire. The sheet metal components 2106 may help to constrain the actuating wire 2108 and also structurally fix the pulley 2102 to the distal joint section 2110. The hinge joints 2104*a* and 2104*b* provide points of rotation for the distal joint section 2110 and are axially aligned with the pulley 2102. FIGS. 21*c* and 21*d* show a cross section of the torque joint with the pulley 2102. In the Figures, the lumen 2112 is bisected due to the centrally aligned pulley 2102.

Figure 21F:
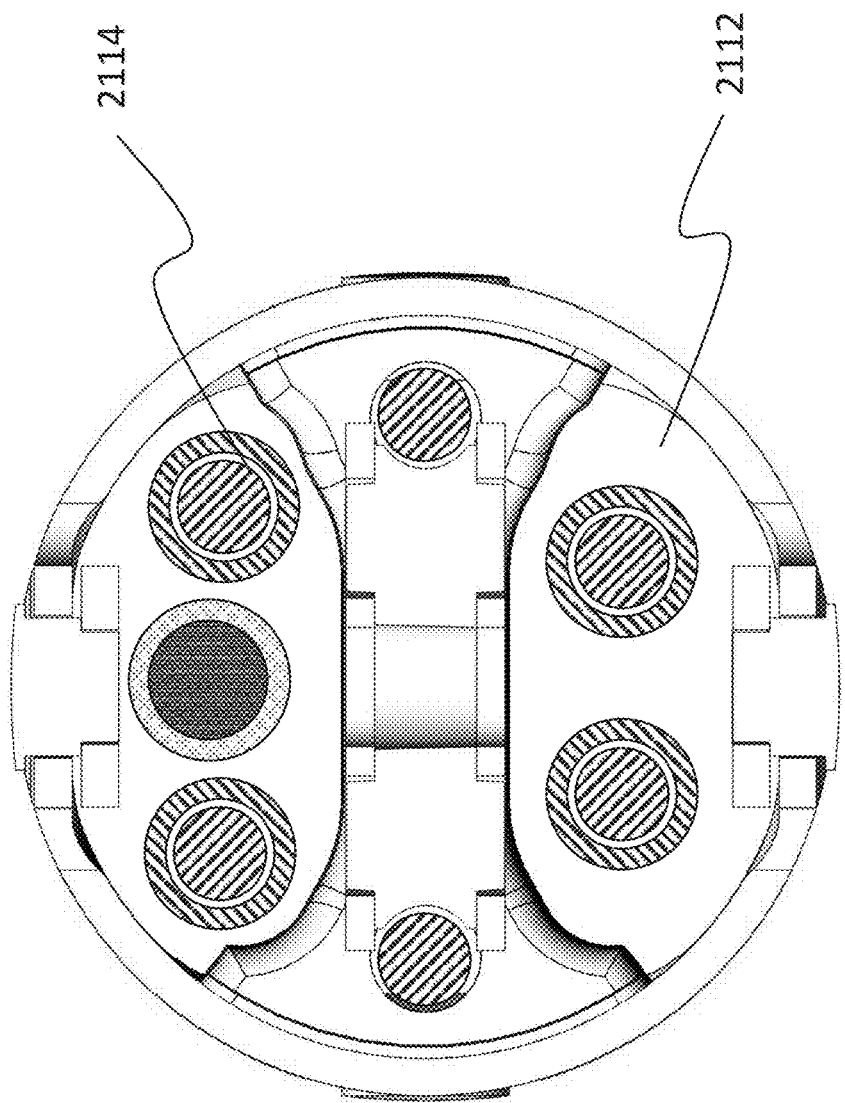
FIG. 21e shows a cross section of a lumen of the flexible elongate member and FIG. 21f shows the cross section of FIG. 21e being rotated 90 degrees clockwise in accordance with the present embodiment.
Figure 21E:
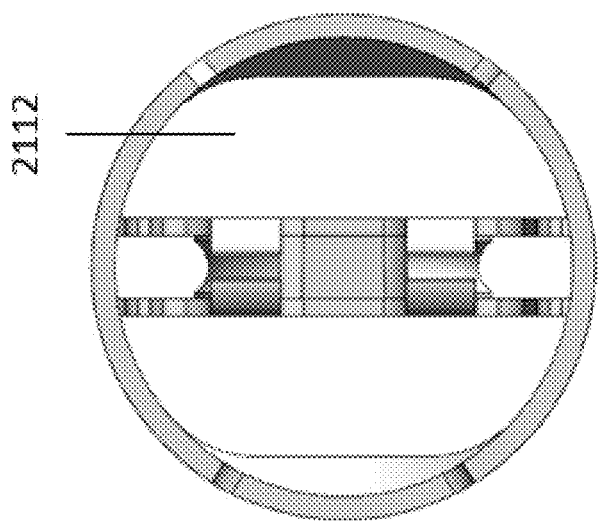

FIG. 21*e* shows a cross section of the lumen 2112 and FIG. 21*f* shows the same cross section being rotated 90 degrees clockwise according to an example embodiment. In the Figures, the configuration reserves space for the pulley 2102 without encumbering the pass-through elements 2114 (not shown in FIG. 21*e*). A centrally aligned pulley allows its diameter to be as large as possible, which increases the mechanical advantage of the joint. The absence of a central rivet pin means that the lumen 2112 is not excessively dissected, which would have reduced lumen cross sectional area available for the pass-through elements 2114. The torque joint of the current invention may also allow the pass-through elements 2114 to undergo less severe bending when the joint is articulated.

Figure 22:
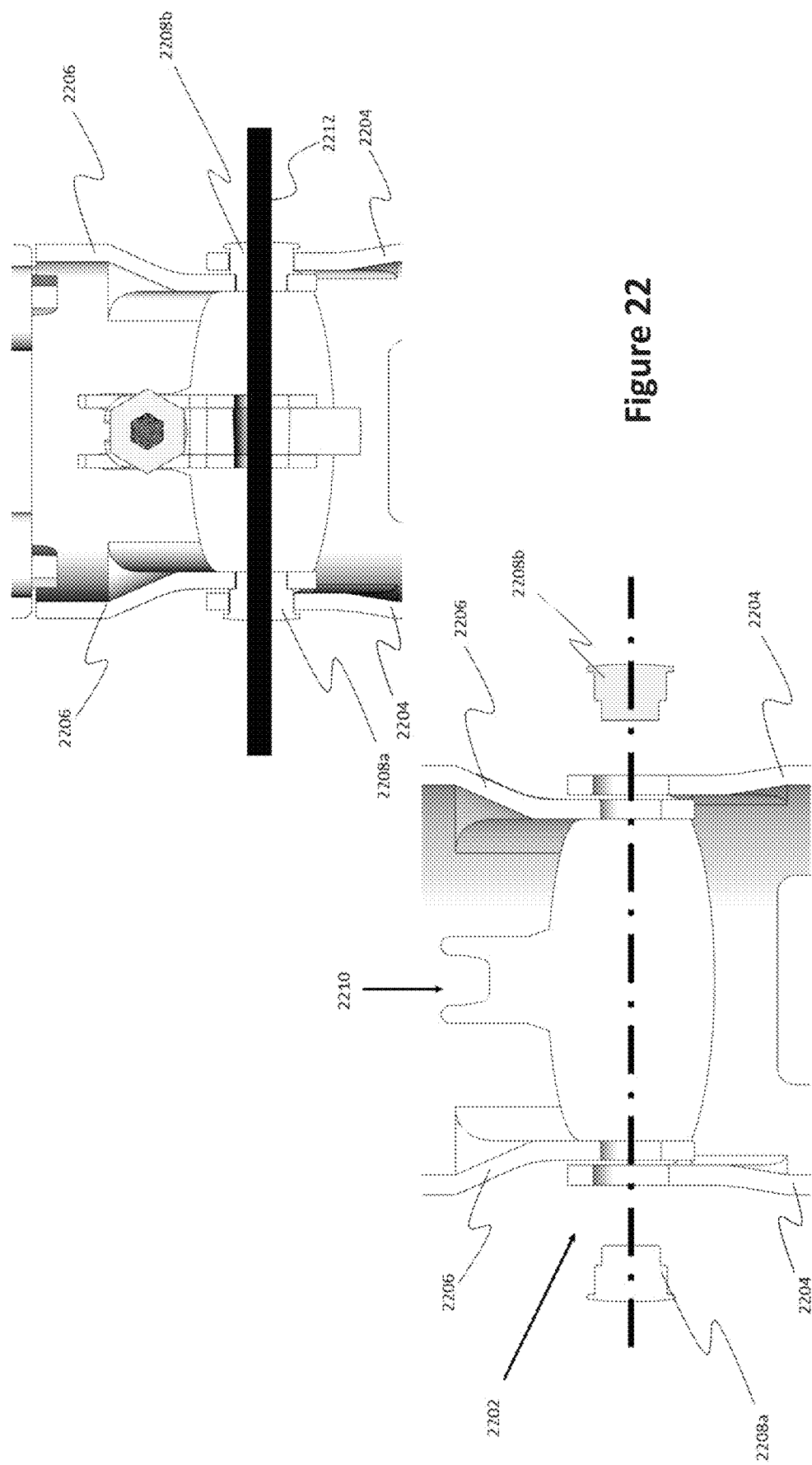
FIG. 22 shows a cross sectional view of a typical hinge joint of the flexible elongate member in accordance with the present embodiment.

FIG. 22 shows a cross sectional view of a typical hinge joint 2202. The joint 2202 may include a proximal segment 2204 and a distal segment 2206 and may be positioned at the robotic member 410 (as shown in FIG. 14). Rotation occurs around the point where both the proximal segment 2204 and the distal segment 2206 overlap. In a preferred embodiment as shown, both the segments 2204, 2206 may be constrained using two separate rivet pins 2208*a* and 2208*b*. This may enable the internal luminal space 2210 to be reserved for other uses.

A clearance fit exists between the pins 2208*a*, 2208*b* and joint segments 2204 and 2206 that allows smooth rotation of the joint. However, such a clearance may prevent the ease of aligning the pivot axes of the two segments 2204, 2206. If the segments are misaligned, there may be difficulty in movement at the extreme ranges of motion. Hence, the pins 2208*a*, 2208*b* may be aligned with each other by means of a bridging insert 2212. Thus, a method may be provided to ensure axial alignment of the two discrete hinge joints through the use of a bridging insert during assembly. The bridging insert can either become part of the joint or can be extracted. In an embodiment as shown in FIG. 22, the insert 2212 may be a rod that runs through holes in the rivet pins 2208*a*, 2208*b* and thus may ensure that the segments are aligned. After the rivet pins 2208*a*, 2208*b* have been welded to the proximal segment 2204 to create a retained joint, the bridging insert 2212 is removed.

In endoscope systems, where a translation actuator is used to translate robotic members 410 in and out of the transport endoscope 320 (see FIG. 2, whereby the robotic members 410 are introduced into the transport endoscope 320 through its proximal end 920, see FIG. 9A), it is advantageous that the translation actuator remains fixed in position when power is removed from the translation actuator. In systems where the translation actuator is back-drivable under expected external forces like gravity or other forces, the robotic members 410 will move in or out of the transport endoscope 320 when power is removed from the actuator. This is especially disadvantageous when uncommanded translation motion of the robotic members 410 causes the robotic members 410 to come into unintentional contact with sensitive tissue. Thus, it is advantageous that the translation actuators of endoscopic systems be non-back drivable when powered down.

Figure 23B:
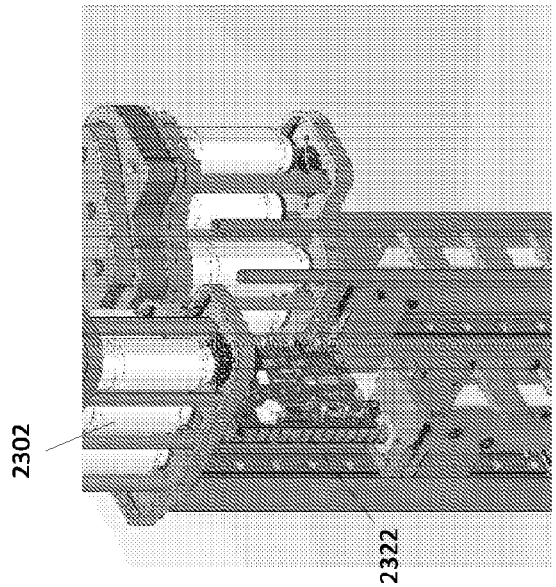
FIG. 23b shows a close-up of the perspective view of FIG. 23a in accordance with the present embodiment.
Figure 23A:
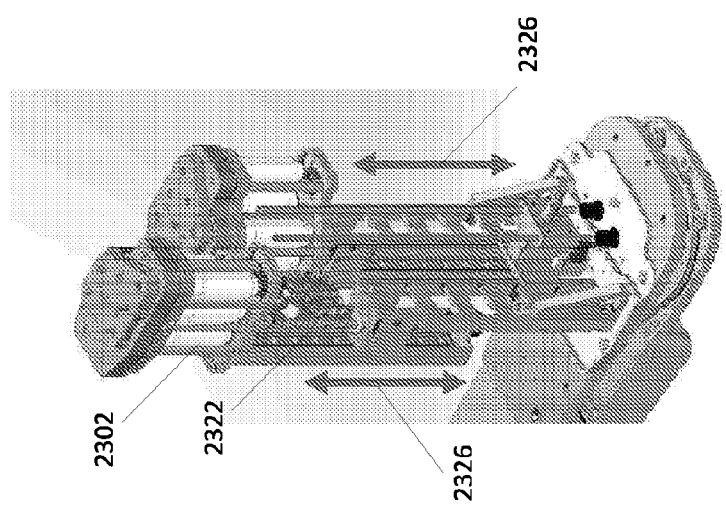

FIG. 23*a* shows a perspective view of a typical translation mechanism of while FIG. 23*b* shows a close-up of the perspective view of the typical translation mechanism. Typical translation actuators often employ low friction drive mechanisms, such as ball screws 2322 to convert rotary motion of an electric motor 2302 to linear motion 2326 of the actuator. Ball screws 2322 are preferred in the industry for the low friction that is consumed, which gives repeatable motion for a given input command. Typical ball screws 2322 include rolling contact elements instead of sliding contact elements and have long service lives due to low wear rates. However, typical ball screws 2322 have at least two characteristics that make them unsuitable for use as translation actuators in an endoscopic system. Firstly, the low friction rolling elements of ball screws 2322 make them back-drivable at forces that are often lower than the expected external loads. Secondly, decreasing the pitch of the ball screw 2322 increases its back-driving resistance. The amount that the ball screw pitch can be lowered is limited as compared to other transmission elements. This is because sufficient room must be reserved in between adjacent pitches to accommodate the rolling elements and their reciprocating guide races.

Figure 23C:
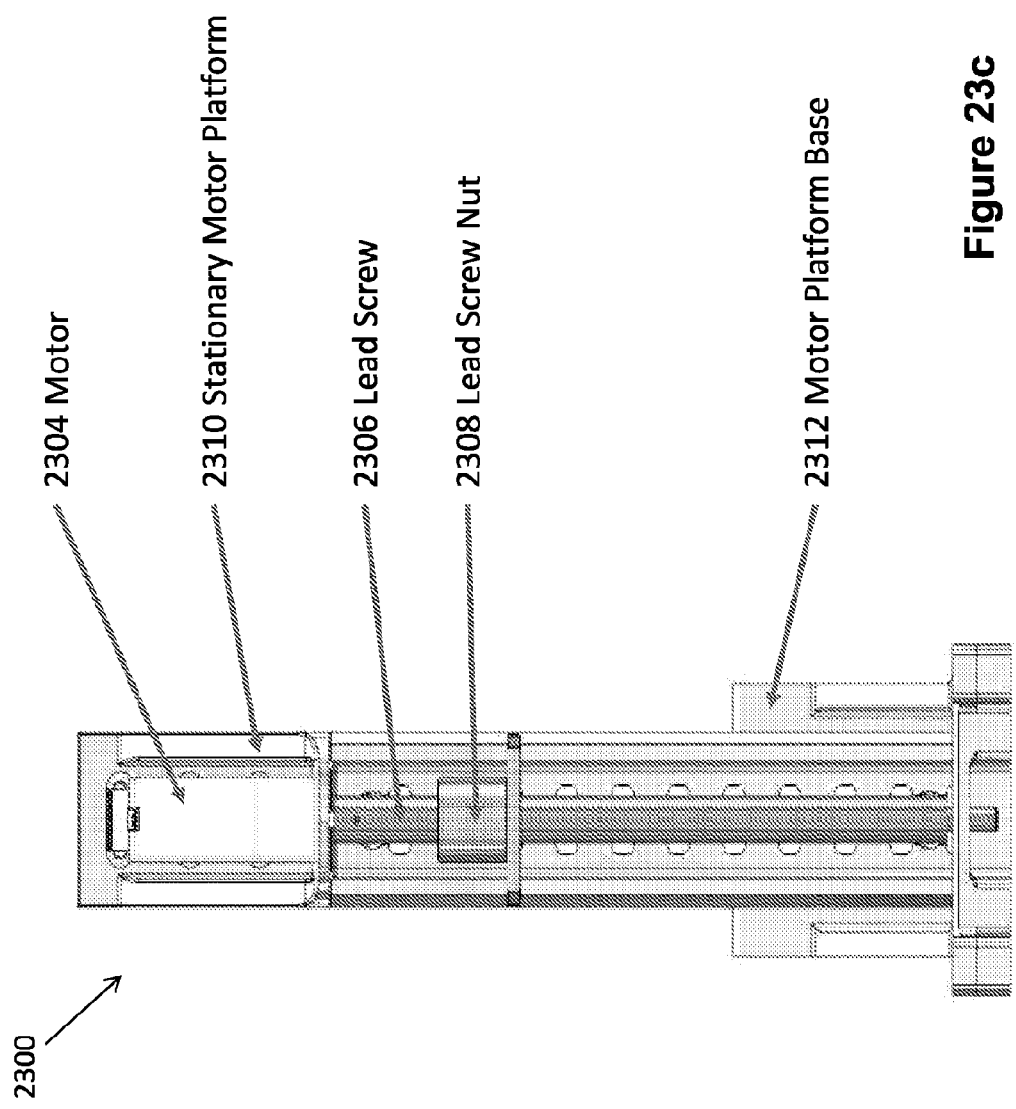

FIGS. 23*c*, 23*d* and 23*e* show cross section views of an implementation of a translation mechanism 2300 that may improve the back-drivability of current industrial linear actuators. As shown in the FIGS. 23*c* to 23*e*, an endoscopic system translation mechanism 2300 includes a rotary motor 2304 and a lead screw 2306 to convert rotary motion of the motor 2304 into translation motion of the robotic members 410 (refer FIG. 2). A lead screw 2306 is used in this embodiment as it has inherently more friction due to the sliding contact between the lead screw 2306 and a lead screw nut 2308 as compared to a ball screw, which has low friction rolling element contact. In addition, a lead screw 2306 can have lower pitch than an equivalently sized ball screw, giving the lead screw 2306 more back-driving resistance. The translation mechanism 2300 may also include a stationary motor platform 2310 for enclosing the motor 2304 and a motor platform base 2312 to support the translation mechanism 2300. FIGS. 23*d* and 23*e* show various positions of the lead screw nut 2308 translated vertically as the motor 2304 rotates the lead screw 2306.

In an alternative embodiment not shown in the figures, the translation mechanism 2300 may include a rotary motor and a ball screw, such that the motor has sufficient internal gear reduction to provide the required back driving resistance. Such an embodiment may be favorable where the higher friction and lower service life of a lead screw are unacceptable in the translation mechanism 2300. A preferred embodiment of such a motor would include a planetary gear reduction or a harmonic drive, both of which allow for large gear reduction ratios in compact sizes.

A further embodiment of the translation mechanism 2300 may include a motor, a ball screw, and an electrically operated friction device that automatically engages to stop motion of the actuator when power is removed from the motor. Such an embodiment may be favorable when the higher friction and lower service life of a lead screw are unacceptable, and where a large gear reduction within the motor would result in an unacceptably slow translation speed. The preferred embodiment of such a friction device is a rotary electromagnetic brake connected to the motor shaft or the ball screw.

An endoscope docking system may include the docking station 500, the transport endoscope 320 and the associated valve controller box 348 (as shown in FIG. 2). It is advantageous to adjust a height of the endoscope docking system to accommodate different patient table heights as well as different clinician heights. In addition, it is also advantageous to secure the endoscope docking system once it is adjusted to a desirable height. Due to safety reasons, the endoscope docking system must remain secure at the desirable height to avoid sudden and unexpected changes during endoscopy.

There are currently a variety of simple mechanisms that could provide an adjustable height function for the endoscope docking system. One example of such a mechanism includes a simple bolting interface with multiple bolting locations of different heights that provides adjustability but may require the use of tools to perform the adjustment and an extra person to support the weight of the mechanism while it is being adjusted. This makes adjustment of a bolting interface during the procedure cumbersome and impractical. Other adjustable height mechanisms such as a mechanically operated vertical screw adjuster or a mechanically operated hydraulic lift cylinder may be employed. It is however impractical to locate the mechanical control of these devices near the user's hand location on the control body of the attached endoscope or near the user's foot due to the large number of mechanical linkages required to transmit the motion to the desired location. This means that the user must stop what they are doing and move over to the position of the controls and then move back to their original location to assess whether the adjustment was sufficient. This adds delay and inconvenience to the user.

Figure 24A:
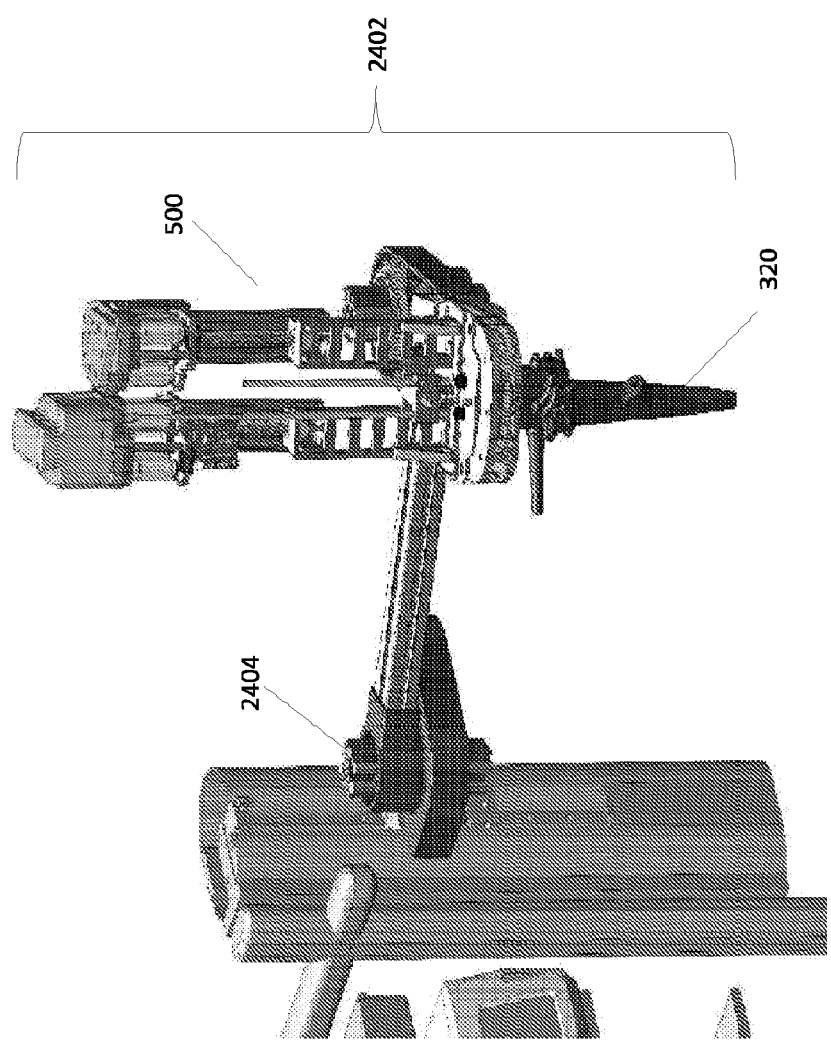
FIG. 24a shows a perspective view of a typical electrically operated height adjustment mechanism of an endoscope docking system in accordance with the present embodiment.

Another solution may include the use of an electrically operated actuator to adjust the height of the endoscope docking system based on inputs from the user via a control interface. FIG. 24a shows a perspective view of a typical electrically operated height adjustment mechanism of an endoscope docking system 2402. The electric actuator 2404 in this mechanism must reliably support and manipulate the entire weight of the endoscope docking system 2402. Due to the large size and weight of the endoscope docking system 2402, the cost of the electric actuator 2404 is also high. Thus, even though an electrically operated actuator 2404 gives more freedom on the location of the user controls, but it also adds significant cost to the endoscopy system.

Herein disclosed are mechanisms that may eliminate the inconvenience of existing mechanical adjustment mechanisms and may provide a lower cost than electric actuator systems. The mechanisms disclosed may include a weight compensation device and an electrically-operated locking device. The weight compensation device may offset the majority of the weight of the endoscope docking system. The remainder of the weight is flexibly hung so as to be easily vertically adjustable without straining. The weight compensation device may also include a height adjustment mechanism to adjust the height of the endoscope docking system.

The electrically-operated locking device may include a controller and user controls. Being electronic, the user controls can be located near to hand or foot locations, e.g. with reference to FIG. 7, near the PID 702 or foot pedals of the master section. The preferred user controls consist of either a hand-operated button, or a foot-operated switch. The devices default to the locked state and are only unlocked during activation of the user controls.

Figure 24B:
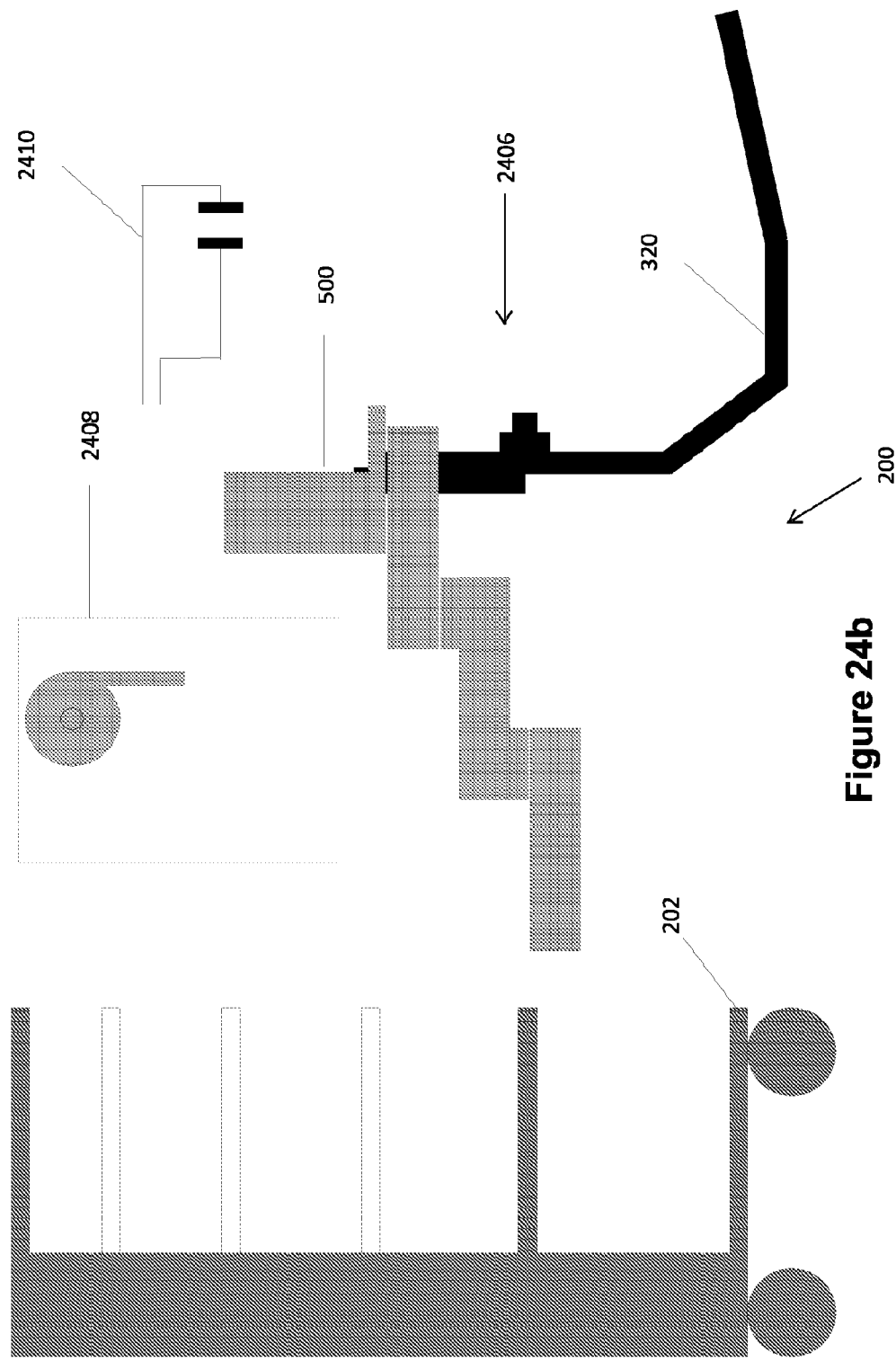
FIG. 24b shows a side view of a first implementation of the slave section of FIG. 2 in accordance with the present embodiment.

FIG. 24b shows a side view of the slave section 200 of FIG. 2 incorporating a weight compensation device and an electrically-operated locking device, both in accordance with a first implementation. As shown in the FIG. 24b, the slave section 200 includes the patient-side cart 202, an endoscope docking system 2406, a height adjustment mechanism 2408 and a linear electromagnetic brake 2410. The endoscope docking system 2406 includes the docking station 500 and the transport endoscope 320 (as shown in FIG. 2). In this implementation, the height adjustment mechanism 2408 may include a constant force spring from which the endoscope docking system 2406 is directly hung. The force of the constant force spring is customized to be substantially similar to the weight of the endoscope docking system's 2406 heaviest configuration.

Figure 24C:
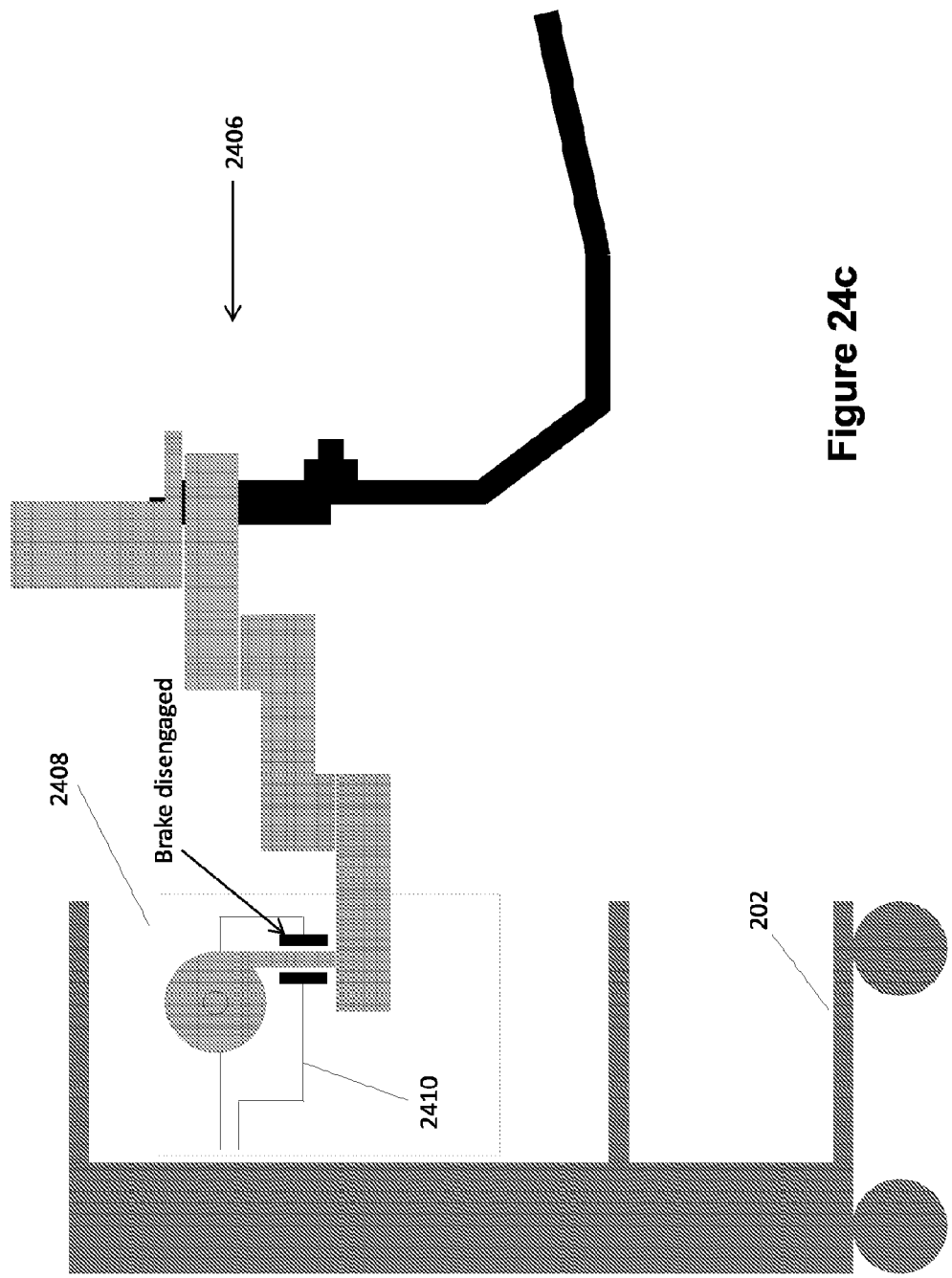
FIG. 24c shows a side view of the first implementation with a disengaged electromagnetic brake when the endoscope docking system is at its highest position in accordance with the present embodiment.

As shown in FIG. 24c, the endoscope docking system 2406 is at its highest position with the linear electromagnetic brake 2410 disengaged. This allows height adjustment of the endoscope docking system 2406 by the height adjustment mechanism 2408 while maintaining the weight of the endoscope docking system 2406.

FIG. 24d shows the endoscope docking system 2406 at its highest position with the linear electromagnetic brake 2410 engaged. After the endoscope docking system 2406 is adjusted to a desirable height, the engaged linear electromagnetic brake 2410 firmly secures the endoscope docking system 2406 to avoid sudden and unexpected changes during endoscopy which may endanger the patient. More specifically, the linear electromagnetic brake 2410 may directly engage the endoscope docking system 2406 using friction to prevent vertical movement of the endoscope docking system 2406.

Figure 24E:
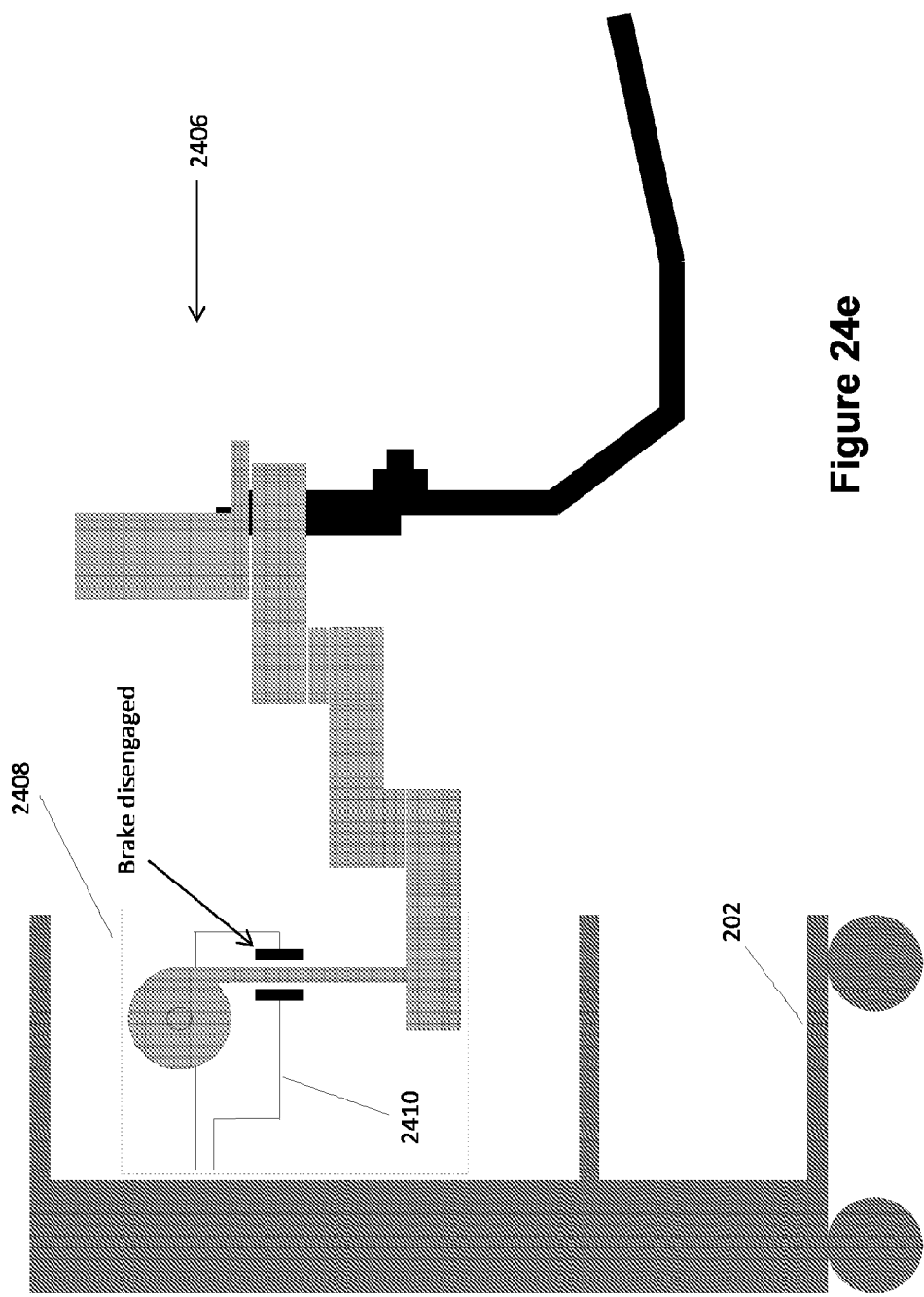
FIG. 24e shows a side view of the first implementation with a disengaged electromagnetic brake when the endoscope docking system is at its lowest position in accordance with the present embodiment.
Figure 24F:
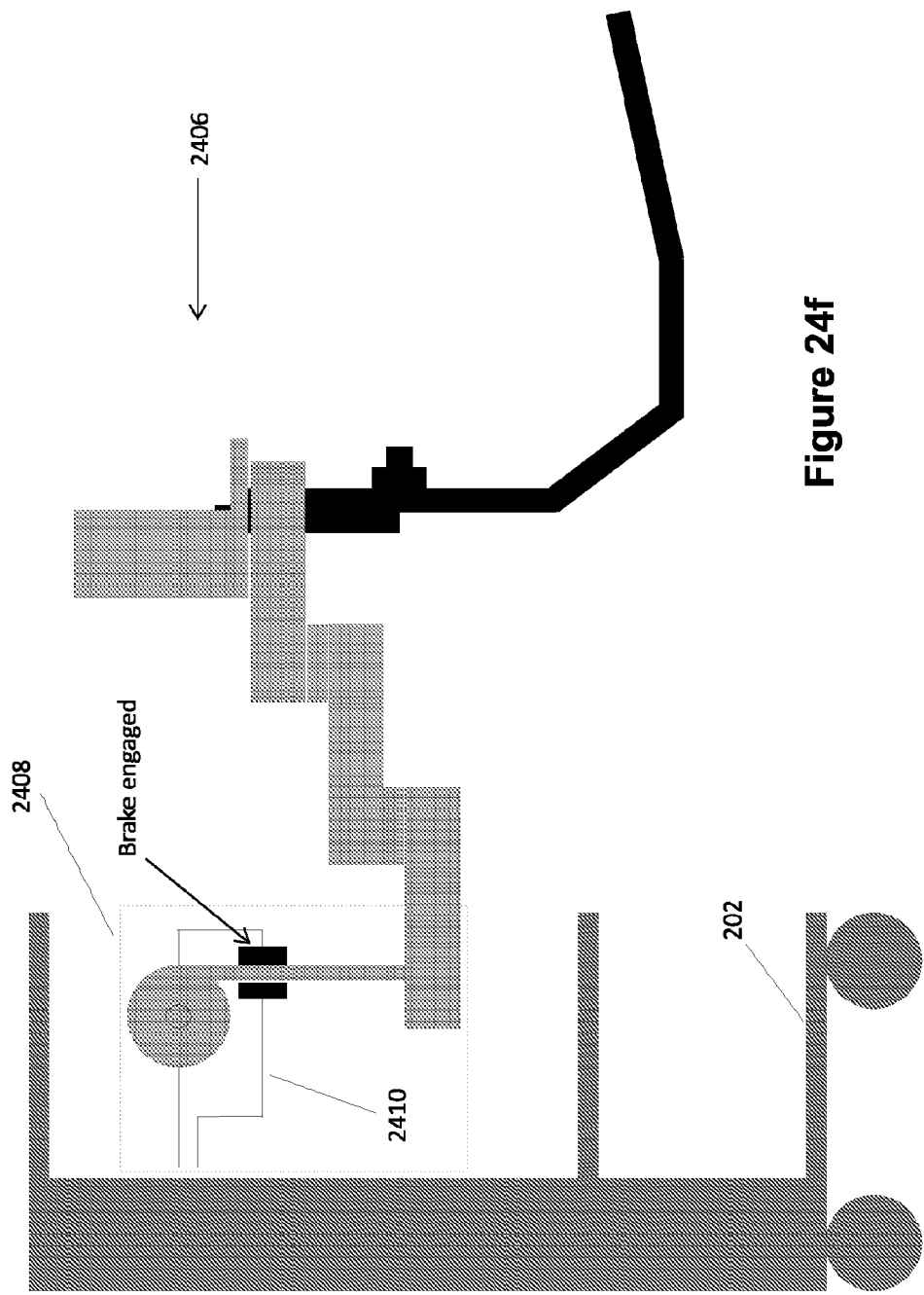
FIG. 24f shows a side view of the first implementation with an engaged electromagnetic brake when the endoscope docking system is at its lowest position in accordance with the present embodiment.

The slave section 200 may include a linear electromagnetic engaging spline or ratchet (not shown in the Figures) that directly engages the endoscope docking system 2406 using interlocking components to prevent vertical movement of the endoscope docking system 2406. Examples of interlocking components include actuators, gears and/or valves. FIGS. 24e and 24f show the electromagnetic brakes 2410 at the disengaged and engaged positions respectively when the endoscope docking system 2406 is at its lowest point.

Figure 24G:
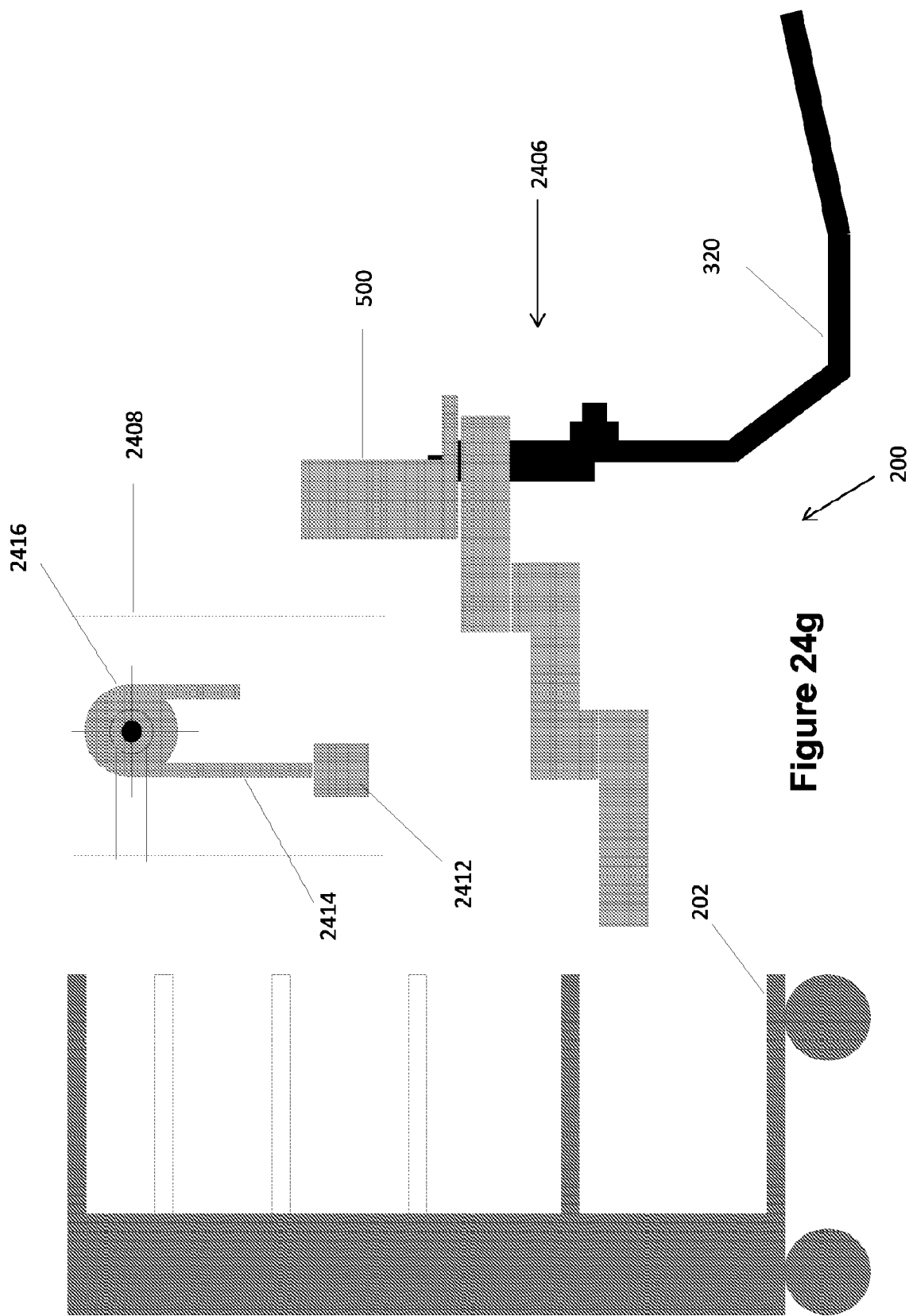
FIG. 24g shows a side view of a second implementation of the slave section of FIG. 2 in accordance with the present embodiment.

FIG. 24g shows a side view of the slave section 200 of FIG. 2 incorporating a weight compensation device and an electrically-operated locking device, both in accordance with a second implementation. As shown in the FIG. 24g, the slave section 200 includes the patient-side cart 202, an endoscope docking system 2406 and a height adjustment mechanism 2408. The endoscope docking system 2406 includes the docking station 500 and the transport endoscope 320 (as shown in FIG. 2).

Figure 24H:
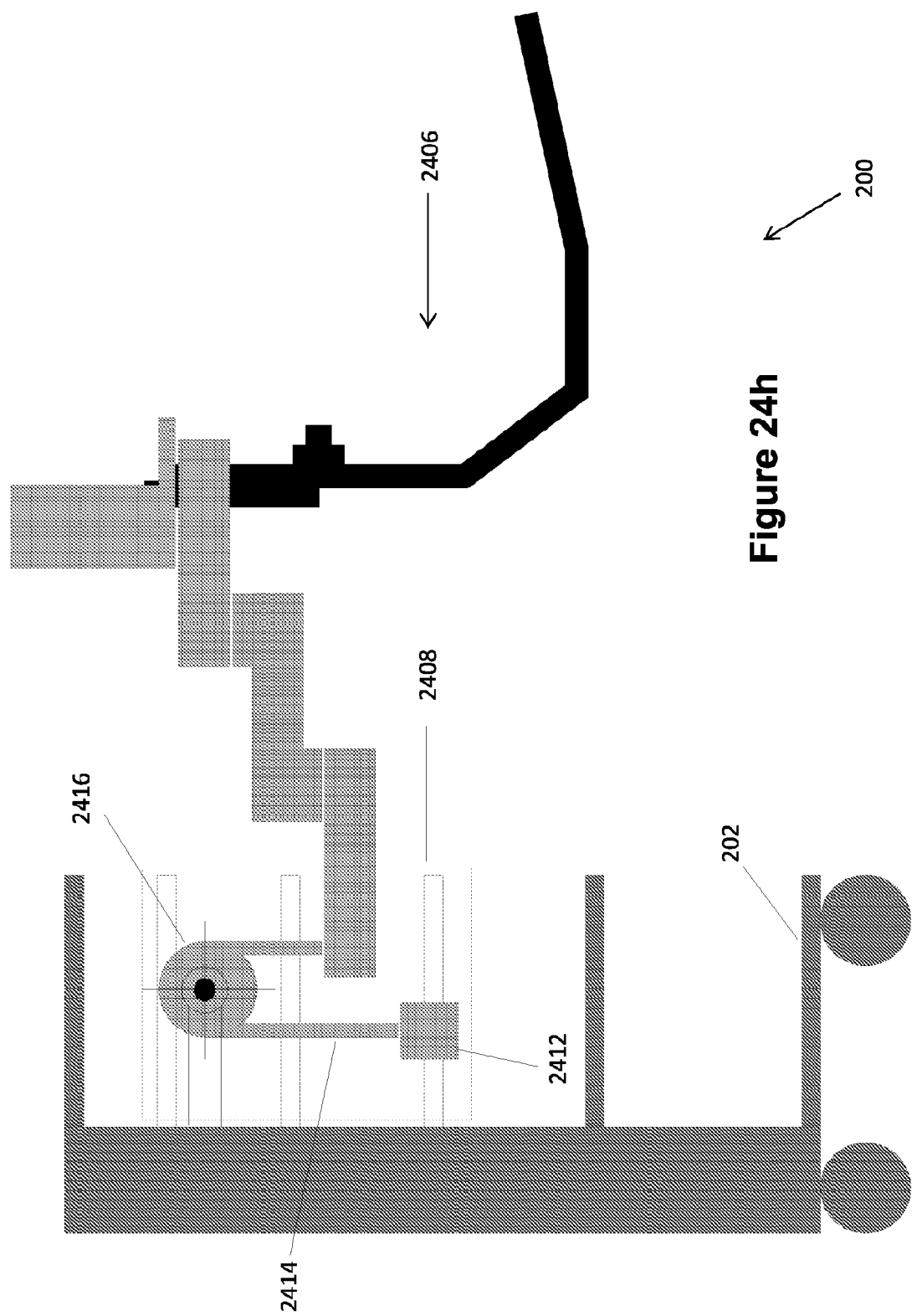
FIG. 24h shows a side view of the second implementation when the endoscope docking system is at its highest position in accordance with the present embodiment.
Figure 24I:
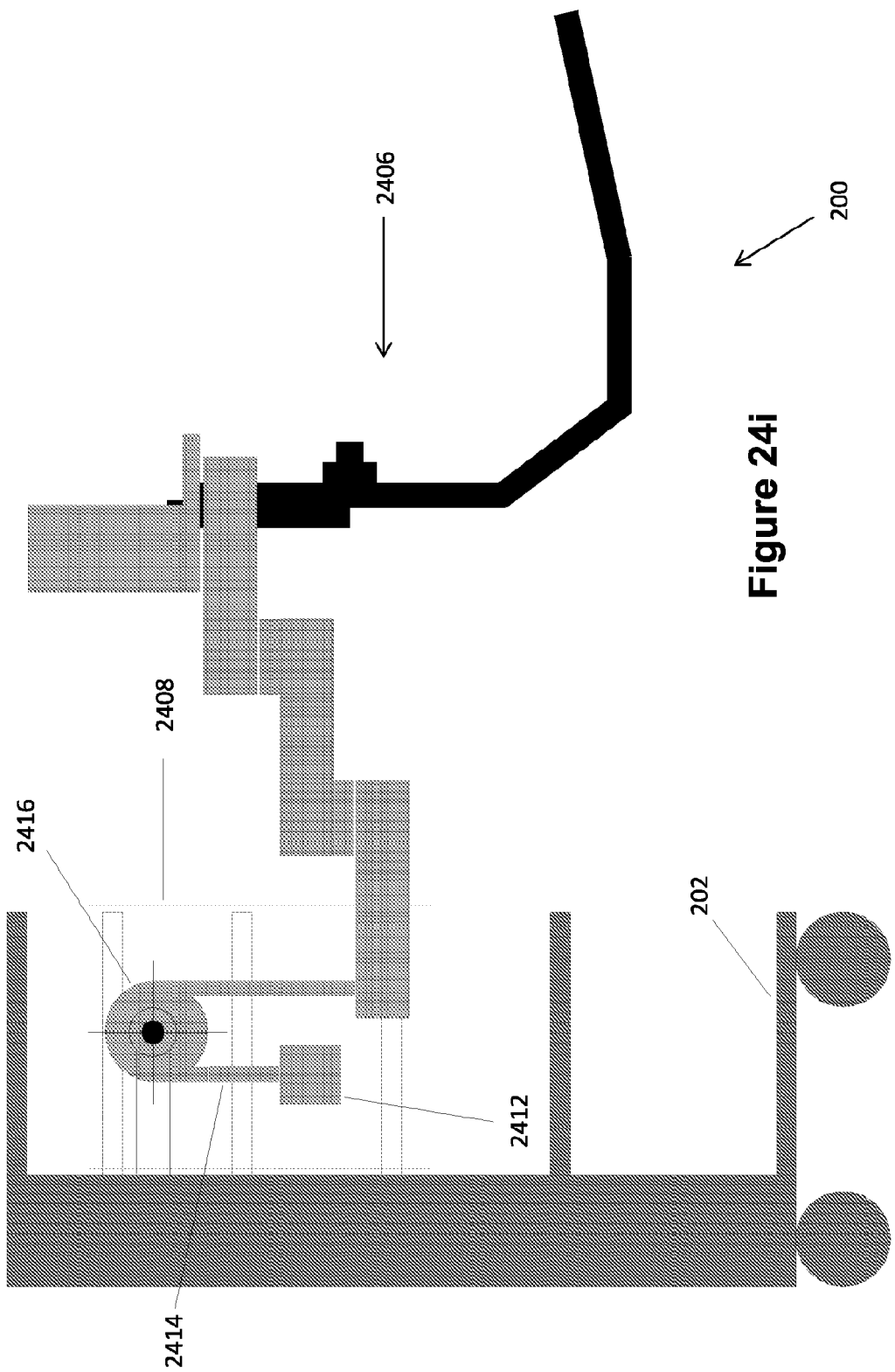
FIG. 24i shows a side view of the second implementation when the endoscope docking system is at its lowest position in accordance with the present embodiment.

In this second implementation, the height adjustment mechanism 2408 may be a counter-weight and pulley system, where the counterweight 2412 is substantially similar in weight to the endoscope docking system 2406. An elongate flexible member 2414 connects the counterweight 2412 to the endoscope docking system 2406 in a way such that the elongate flexible member 2414 is routed up and over said pulley 2416. The elongate member 2414 may be inelastic and may be made of anti-slip material so that there is no slippage between the elongate member 2414 and the pulley 2416 as the docking system 2406 undergoes vertical motion. Preferred embodiments of the pulley 2416 and elongate flexible member 2414 may consist of either a cog tooth belt and a cog tooth pulley, or a chain sprocket and a chain. In addition, the height adjustment mechanism 2408 may include a rotational electromagnetic brake (not shown) that is applied to the pulley 2416 to which the elongate member 2414 engages. FIGS. 24h and 24i each respectively show an implementation of the counterweight and pulley system when the endoscope docking system 2406 is at its highest position and lowest position.

It will be appreciated by a person skilled in the art that numerous variations and/or modifications may be made to the present invention as shown in the embodiments without departing from a spirit or scope of the invention as broadly described. The embodiments are, therefore, to be considered in all respects to be illustrative and not restrictive.

What is claimed is:

1. An endoscope system comprising:
an endoscope having a hollow tube formed therein, wherein the endoscope has a first end coupleable to a docking station and a second distal end;
a flexible elongate member for insertion through the hollow tube, wherein the flexible elongate member has a first end for operational control and a second distal end for operation of robotic members at the distal end of the endoscope;
one or more actuators coupleable to the flexible elongate member at the first end thereof, the one or more actuators translatable in a direction parallel to a central axis of the hollow tube to allow fine movement of the second distal end of the flexible elongate member during operation;
an anti-buckling tube arranged with respect to the hollow tube at the first end of the endoscope, the flexible elongate member inserted through the anti-buckling tube downstream of the one or more actuators to prevent buckling of the flexible elongate member during translation of the one or more actuators; and
one or more supports coupling the anti-buckling tube to the one or more actuators, wherein the actuators are housed within a motor housing, the one or more supports coupling the anti-buckling tube to the motor housing, wherein the motor housing comprises a stationary portion and a translatable portion which translates the one or more actuators in the direction parallel to the central axis of the hollow tube, and wherein at least a first portion of the one or more supports couple the anti-buckling tube to the stationary portion of the motor housing.

2. The endoscope system in accordance with claim 1 wherein the anti-buckling tube is situated between the one or more actuators and the first end of the endoscope.

3. The endoscope system in accordance with claim 1 wherein the one or more supports comprise magnetic means or mechanical means for coupling the anti-buckling tube to the motor housing.

4. The endoscope system in accordance with claim 1 wherein the anti-buckling tube comprises two or more tubes arranged in a telescopic structural arrangement such that a first one of the two or more tubes has a larger diameter than a second one of the two or more tubes, and wherein the first portion of the one or more supports couples the first one of the two or more tubes of the anti-buckling tube to the stationary portion of the motor housing and a second portion of the one or more supports couples the second one of the two or more tubes of the anti-buckling tube to the translatable portion of the motor housing.

5. The endoscope system in accordance with claim 1 wherein the anti-buckling tube comprises two or more tubes arranged in a telescopic structural arrangement such that a first one of the two or more tubes has a smaller diameter than a second one of the two or more tubes, and wherein the first portion of the one or more supports couples the first one of the two or more tubes of the anti-buckling tube to the stationary portion of the motor housing and a second portion of the one or more supports couples the second one of the two or more tubes of the anti-buckling tube to the translatable portion of the motor housing.

6. The endoscope system in accordance with claim 1 wherein the anti-buckling tube is flared at one or both ends.

7. The endoscope system in accordance with claim 1 wherein at least a portion of the anti-buckling tube has a rigid structure.

8. The endoscope system in accordance with claim 7 wherein the at least a portion of the anti-buckling tube that has a rigid structure is adjacent to the first end of the flexible elongate member where it couples to the one or more actuators.

9. The endoscope system in accordance with claim 1 wherein the anti-buckling tube is composed of corrosion resistant metal or polymer.

10. The endoscope system in accordance with claim 1 wherein the one or more supports detachably couple the anti-buckling tube to the one or more actuators.

* * * * *